(12) United States Patent  
Li

(10) Patent No.: US 7,755,775 B1
(45) Date of Patent: Jul. 13, 2010

(54) BROADBAND OPTICAL METROLOGY WITH REDUCED WAVE FRONT DISTORTION, CHROMATIC DISPERSION COMPENSATION AND MONITORING

(75) Inventor: Guoguang Li, Fremont, CA (US)

(73) Assignee: n&k Technology, Inc., San Jose, CA (US)

( * ) Notice: Subject to any disclaimer, the term of this patent is extended or adjusted under 35 U.S.C. 154(b) by 518 days.

(21) Appl. No.: 11/542,953

(22) Filed: Oct. 3, 2006

(51) Int. Cl.
G01B 11/14 (2006.01)
G01J 3/02 (2006.01)
G01J 3/42 (2006.01)

(52) U.S. Cl. .................. 356/625; 356/445; 356/319; 250/339.07; 250/339.11

(58) Field of Classification Search ......... 356/364–369, 356/237.2, 625–632, 445, 309–310, 317–320, 356/237.1, 237.3, 239.1–239.8; 250/327, 250/306–307, 559.27, 225, 339.07, 339.11
See application file for complete search history.

(56) References Cited

U.S. PATENT DOCUMENTS

| | | | |
|---|---|---|---|
| 4,362,364 A | 12/1982 | Smith | |
| 5,274,497 A * | 12/1993 | Casey | 359/364 |
| 5,305,074 A * | 4/1994 | Feldman | 356/512 |
| 5,764,365 A | 6/1998 | Finarov | |
| 5,880,831 A * | 3/1999 | Buermann et al. | 356/319 |
| 5,991,022 A | 11/1999 | Buermann et al. | |
| 6,075,612 A | 6/2000 | Mandella et al. | |
| 6,128,085 A | 10/2000 | Buermann et al. | |
| 6,133,986 A * | 10/2000 | Johnson | 355/67 |
| 6,181,427 B1 | 1/2001 | Yarussi et al. | |
| 6,392,756 B1 * | 5/2002 | Li et al. | 356/632 |
| 6,456,376 B1 | 9/2002 | Liphardt et al. | |
| 6,611,330 B2 | 8/2003 | Lee et al. | |
| 6,657,736 B1 * | 12/2003 | Finarov et al. | 356/625 |
| 6,734,967 B1 | 5/2004 | Piwonka-Corle et al. | |
| 6,753,961 B1 | 6/2004 | Norton et al. | |
| 6,785,319 B1 | 8/2004 | Ariga | |
| 6,842,251 B1 | 1/2005 | Holden | |
| 6,859,275 B2 * | 2/2005 | Fateley et al. | 356/330 |
| 6,870,609 B2 | 3/2005 | Watkins et al. | |
| 6,891,628 B2 | 5/2005 | Li et al. | |
| 7,139,365 B1 * | 11/2006 | Janik | 378/70 |
| 7,292,331 B2 * | 11/2007 | Vertoprakhov | 356/237.5 |
| 7,349,103 B1 * | 3/2008 | Balooch et al. | 356/601 |
| 7,369,233 B2 * | 5/2008 | Nikoonahad et al. | 356/369 |
| 7,397,030 B1 * | 7/2008 | Balooch et al. | 250/306 |
| 2004/0047053 A1 | 3/2004 | Li | |

* cited by examiner

*Primary Examiner*—Sang Nguyen
(74) *Attorney, Agent, or Firm*—Lumen Patent Firm

(57) ABSTRACT

Apparatus and method for examining a sample with a broadband radiation while preserving a small spot and low wave front distortion. The apparatus has a broadband source for generating the broadband radiation and a first reflective optics that employ toroidal mirrors that are barrel or donut-shaped and may be placed in a crossed or parallel arrangement for producing a broadband test beam that is guided to the sample such that it is incident on it at a small spot. A sampling aperture is provided for filtering a certain center portion from the broadband test beam. A second reflective optics is provided for shaping a reflected response beam from the broadband radiation that is reflected from the spot. The response beam is delivered by second reflective optics to a detector for examination. The apparatus and method can be applied to improve wave front distortion in reflectance measurements and for performing transmittance measurements with chromatic distortion compensation. The method and apparatus further provide for efficient monitoring of the broadband test beam.

46 Claims, 21 Drawing Sheets

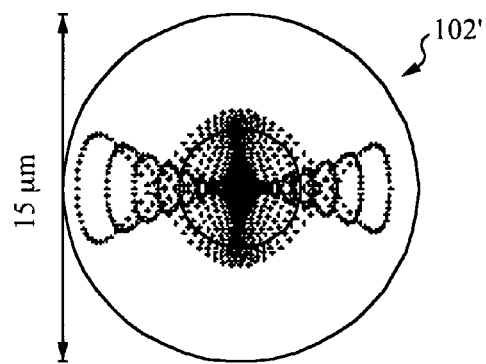
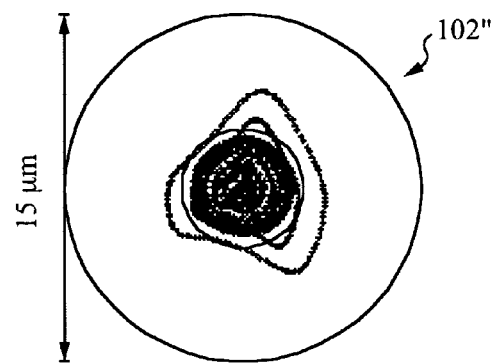
FIG. 7A  FIG. 7B
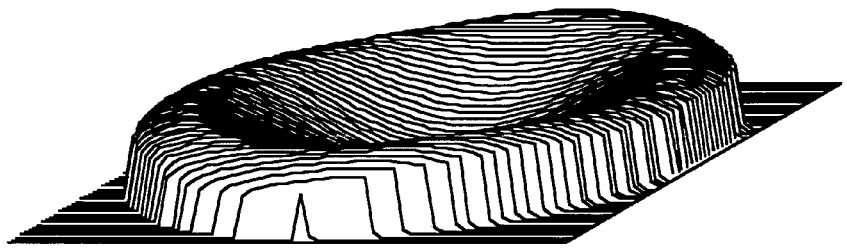
FIG. 8
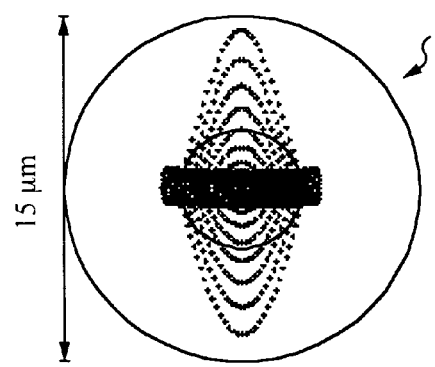
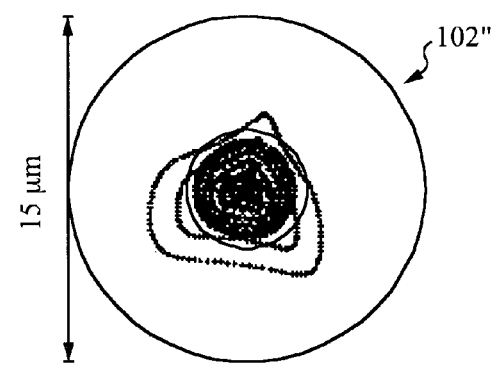
FIG. 9A  FIG. 9B

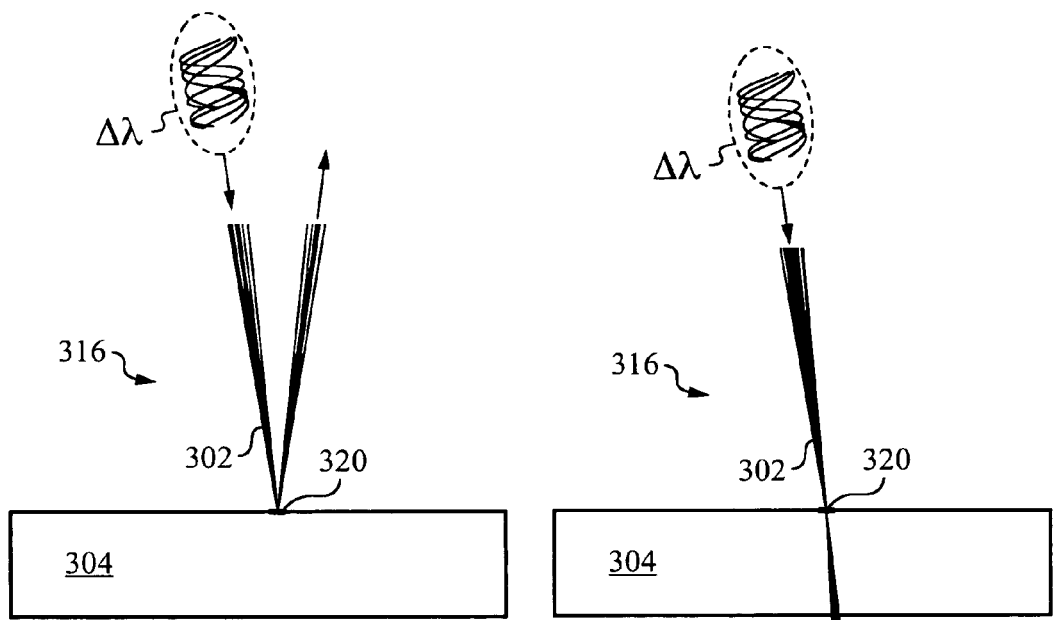
FIG. 23A　　　FIG. 23B
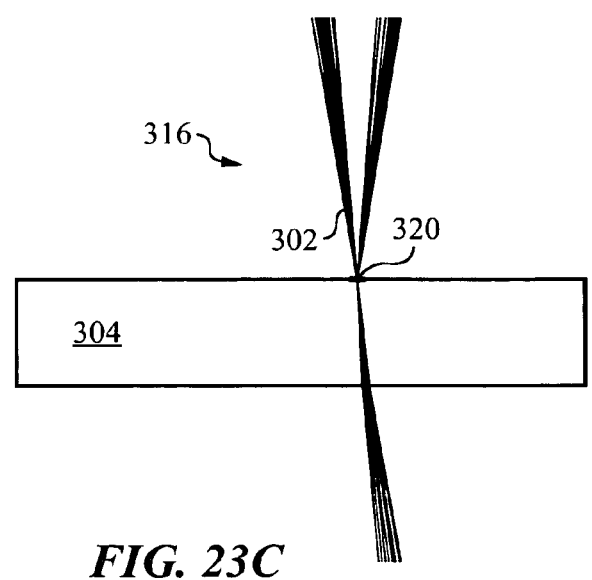
FIG. 23C

BROADBAND OPTICAL METROLOGY WITH REDUCED WAVE FRONT DISTORTION, CHROMATIC DISPERSION COMPENSATION AND MONITORING

FIELD OF THE INVENTION

This invention relates generally to systems and methods for optical metrology employing broadband radiation, and more specifically to systems and methods that employ broadband metrology using optics that reduce wave front distortion at the examination spot and compensate for chromatic dispersion while also permitting beam monitoring.

BACKGROUND ART

There are a number of optical metrology systems and applications including scatterometry, polarimetry, spectroscopy and ellipsometry that require a broadband test beam. The large bandwidth or wavelength range $\Delta\lambda$ of the radiation used in these test beams imposes a set of constraints on the optical system and on a number of its operating parameters. The most important constraints are the increasing wave front distortion encountered when employing refractive optics in apparatus for these applications as well as chromatic dispersion.

To limit chromatic dispersion, a number of prior art references teach the use of all-reflective optics, i.e., various types of reflectors or mirrors. For example, U.S. Pat. Nos. 5,991,022 and 6,128,085 to Buermann et al. teach the use of specific types of mirrors, namely toroidal ones in a spectroscopic apparatus. The use of toroidal mirrors for reflectance measurements in particular is also taught by Mandella et al. in U.S. Pat. No. 6,075,612. U.S. Pat. No. 6,181,427 to Yarussi et al. teaches a compact optical reflectometer system that employs flat mirrors and U.S. Pat. Appl. 2004/0047053 to Li teaches the use of ellipsoidal reflectors for coupling light from a source to a target. U.S. Pat. No. 6,611,330 to Lee et al. illustrates the use of a mirror system for performing polarimetric measurements that may be combined with ellipsometry using a beam of broadband radiation.

In addition to managing chromatic dispersion, optical systems frequently require spatial filtering in order to ensure that only radiation coming from a certain place is detected or imaged by the system. The most well-known approach to spatial filtering involves the use of apertures or pinholes. These are used extensively in fields such as confocal microscopy, e.g., as described in U.S. Reissue 32,660 to Lindow et al. and U.S. Pat. No. 6,870,609 to Watkins et al. Prior art optical metrology apparatus also employ spatial filtering, for example in the field of ellipsometry, as shown in U.S. Pat. No. 6,456,376 by Liphardt et al. Still other examples of spatial filtering in a metrology device that operates in reflectance mode, transmittance mode or mixed mode are found in U.S. Pat. No. 6,842,251 to Holden et al.

A more specific subset of optical metrology applications involves measuring samples with broadband radiation that is transmitted through the sample. Such measurements can be performed when the samples or substrates under study are transparent or semi-transparent. For general information about transmission metrology the reader is referred to U.S. Pat. No. 6,891,628 to Li et al. Still other optical systems that employ reflective optics for measuring samples such as wafers are described in U.S. Pat. No. 5,764,365 to Finarov and U.S. Pat. No. 6,734,967 to Piwonka-Corle et al.

Unfortunately, although some of the above prior art approaches manage to reduce chromatic dispersion, they are not capable of examining samples with small spots exhibiting low wave front distortion. Furthermore, the prior art systems are not able to combine the low wavelength distortion constraint with compensation for chromatic dispersion of light transmitted through the sample and contemporaneous and efficient beam monitoring. This is especially true in systems that perform transmittance measurements and in which the chromatic dispersion affects broadband radiation that is incident on the sample at off-normal angles.

OBJECTS AND ADVANTAGES

In view of the above prior art limitations, it is an object of the present invention to provide an apparatus and method for examining samples with a small beam spot that exhibits reduced wave front distortion. Specifically, it is an object of the invention to provide appropriate reflective optics and spatial filtering to achieve reduced wave front distortion and reduced chromatic distortion.

It is another object of the invention to ensure that the apparatus and method can be employed in optical reflectance as well as combined reflectance and transmittance measurements of bulk samples as well as samples with miniature features, such as semiconductor wafers bearing photolithographically produced integrated circuits.

It is a further object to provide an apparatus and method for examining samples with a transmitted broadband beam that is compensated for chromatic dispersion manifesting in chromatic walk-off or spreading of the transmitted beam as well as chromatic aberration.

It is still another object of the invention to provide an apparatus and method for examining a sample with a broadband beam that exhibits low chromatic aberration while simultaneously permitting direct monitoring of the broadband beam.

These and other objects and advantages of the invention will become apparent from the ensuing description.

SUMMARY OF THE INVENTION

The objects and advantages of the invention are addressed by an apparatus for examining a sample with a broadband radiation. The apparatus has a broadband source for generating the broadband radiation spanning a wavelength range $\Delta\lambda$ and a first reflective optics for shaping the broadband radiation into a broadband test beam. The first optics guides the broadband test beam such that it is incident on the sample at a spot with a certain cone angle $\chi$. A second reflective optics is provided for shaping a reflected response beam from the broadband radiation that is reflected from the spot. The reflected response beam is delivered by second reflective optics to a first detector for examination.

In a preferred embodiment, the first reflective optics employs two toroidal mirrors. Various arrangements of such mirrors are possible including a crossed arrangement, which is preferred. The sampling aperture is positioned between the toroidal mirrors, e.g., in the image plane where the beam waist of the test beam is the smallest. The mirrors themselves can be selected from among barrel-shaped and donut-shaped toroidal mirrors and either the same shape or a combination of the two shapes of mirrors can be employed in the first reflective optics.

The second reflective optics preferably also employ curved mirrors. In one embodiment, the second reflective optics have two symmetrically placed off-axis parabolic mirrors for imaging the spot at the detector. In another embodiment two parallel toroidal mirrors are used by second reflective optics to deliver the reflected response beam to the detector.

The broadband test beam generally spans a wide spectrum or wavelength range $\Delta\lambda$, that can extend from the ultra-violet at 190 nm to the far infra-red at 3,000 nm. The source of the broadband radiation is preferably adjusted to deliver emissions in a Gaussian beam profile or Gaussian cross-section. In such cases the broadband test beam has a Gaussian cross-section and the center portion that is filtered by the sampling aperture should contain at most 67% of the intensity of the broadband test beam.

The apparatus and method of invention can take advantage of various broadband sources, including compound broadband sources that are themselves composed of two or more sources. Using compound sources is particularly efficient when the metrology method requires emission of stable levels of radiation over a very wide wavelength range $\Delta\lambda$. In these cases the individual sources making up the compound source span sub-bands of the range $\Delta\lambda$.

In some embodiments the apparatus is adapted for compensating a chromatic dispersion that is produced in the broadband radiation after it is transmitted through the sample. In order to perform transmittance measurements the apparatus has a third optics for shaping a transmitted response beam of the broadband radiation that is transmitted through the sample after being incident on it at the spot. A second detector is placed under the sample to examine the transmitted response beam. In order for chromatic dispersion compensation to be efficient, the center portion of the broadband test beam filtered by the sampling aperture should be sufficiently small to prevent broadband radiation that undergoes multiple internal reflections within the sample from arriving at the second detector. To ensure this condition, it is advantageous to rely on an entrance aperture that is placed before the second detector in addition to the sampling aperture. For example, the sampling aperture is placed between the two mirrors belonging to the first reflective optics and the entrance aperture is placed right in front of the second detector. In some embodiments further apertures or pinholes can be used.

To perform chromatic compensation the apparatus has an optical compensator that is placed between the sample and the second detector. The compensator has an optical plate that is positioned at a certain tilt relative to the sample. The tilt as well as a thickness of the optical plate relative to the sample can be adjusted to achieve optimal compensation. In addition, the optical compensator can further include a lens. The optical plate compensates the portion of chromatic dispersion that is due to chromatic walk-off and the lens can be used to compensate for the portion of chromatic dispersion that is due to chromatic aberration.

In some embodiments the apparatus is additionally adapted for monitoring the broadband test beam with the aid of the sampling aperture. To accomplish this goal, the sampling aperture has a reflective region surrounding the sampling aperture to reflect a certain peripheral portion of the broadband test beam. A third detector is provided for measuring the peripheral portion that is reflected. A control unit that is in communication with the third detector is used for monitoring the broadband test beam. Preferably, an optic is provided for shaping the reflected peripheral portion of the test beam. The optic can have an imaging optic for imaging the reflective region on the third detector.

In addition, a beam splitter can be provided for separating sub-bands of the peripheral portion of the reflected broadband test beam. For example, the beam splitter can be a visible/ultra-violet (UV) beam splitter for separating the visible from the UV broadband radiation. This may be done in order to enable independent detection of the sub-bands corresponding to the individual sources making up the compound broadband source. In these embodiments the detector can also be compound, i.e., it may consist of separate units designed to individually detect broadband radiation in their corresponding sub-bands.

It is further preferable to shape the broadband test beam in such a way that its cross-section is Gaussian. The peripheral portion of the broadband test beam that is used for monitoring should contain at most 33% of the intensity of the broadband test beam. In other words, the amount of radiation that is used for monitoring purposes should not be excessive and should contain the portion of radiation that is not useful in producing a high quality spot by the toroidal mirrors and the sampling aperture.

The methods of the invention are applied to reflected response beams that are formed from radiation that is reflected from the sample, i.e., the response beams are reflected beams. The methods can also be applied to transmitted response beams that are obtained from broadband radiation that is transmitted through the sample. This may be the case when studying transparent or semi-transparent samples. The methods for chromatic dispersion compensation are applied in detecting the transmitted response beam and in those cases the center portion that is filtered from the broadband test beam should be sufficiently small to prevent broadband radiation undergoing multiple internal reflections in the sample from reaching the second detector. This condition is preferably ensured by using the sampling aperture and an entrance aperture before the second detector. The method is applied to reverse a chromatic walk-off by providing an optical plate at a certain tilt with respect to the sample and also having a certain thickness with respect to the sample. The method is also applied to reverse a chromatic aberration by providing a lens.

When performing reflectance, transmittance or both types of measurements, it is possible to monitor the broadband test beam by surrounding the sampling aperture with a reflective region. The reflective region reflects a certain peripheral portion of the broadband test beam, preferably at most 33% when using broadband test beam with a Gaussian cross-section, to a third detector for measurement and monitoring. The monitoring and control can include closed loop feedback for adjusting the broadband source.

The method of invention is generally practiced in optical metrology situations where the spot needs to have a very uniform wave front. To achieve this goal, the broadband radiation is produced by the source, shaped into the broadband test beam by the first reflective optics and filtered with the sampling aperture such that the test beam is incident in a spot that is adjusted in size. Furthermore, the cone angle $\chi$ of the spot is adjusted to be of the appropriate magnitude for the measurement being performed. The placement of the sampling aperture at the broadband beam waist in the image plane between two crossed toroidal mirrors is preferred in any event.

The use of two parabolic mirrors placed symmetrically off-axis in the second reflective optics is preferred because of their imaging properties. Of course, the spot can also be imaged at the detector when a combination of toroidal mirrors is used. Additional elements for various forms of filtering, as may be required for the optical metrology method being practiced may also be present, e.g., polarizers for polarization filtering.

A detailed description of the preferred embodiments of the invention is presented below in reference to the appended drawing figures.

BRIEF DESCRIPTION OF THE DRAWING FIGURES

Figure 3A:
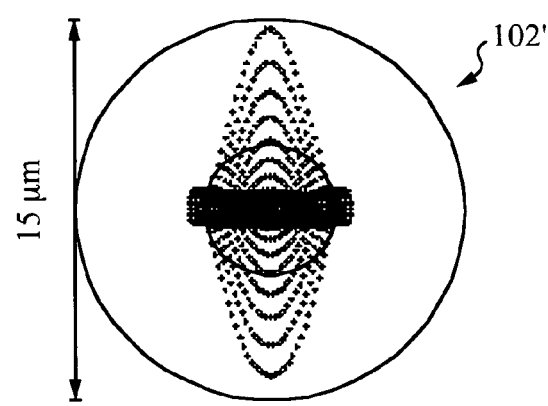
Figure 3B:
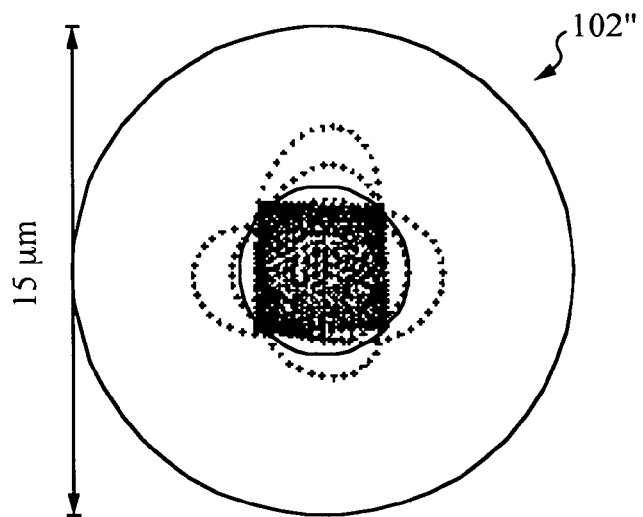

FIGS. 3A-B are spot diagrams illustrating the images of the broadband source after the first and second crossed barrel-shaped toroidal mirrors.

Figure 4:
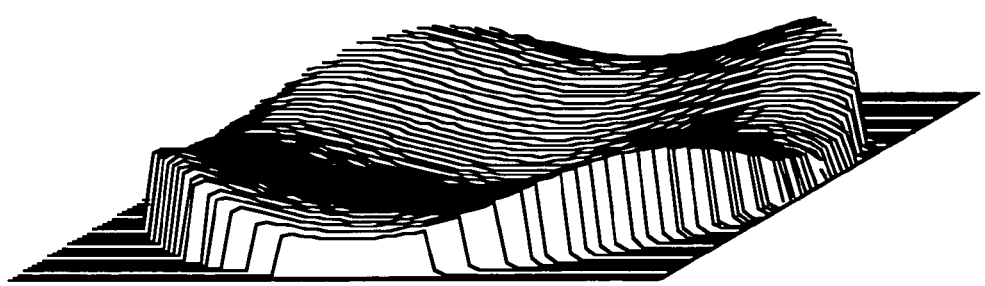

FIG. 4 is a wave front diagram at the spot illuminating the sample in FIG. 3.

Figure 5A:
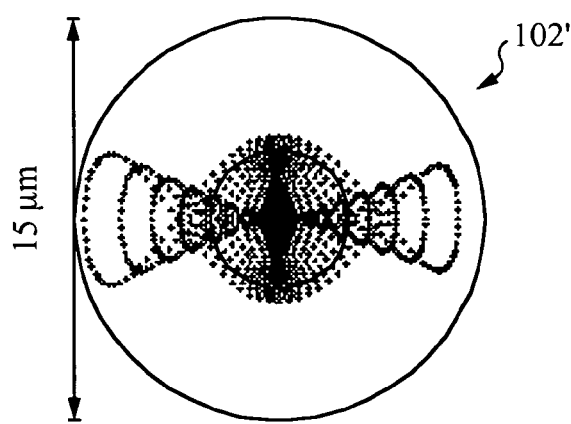
Figure 5B:
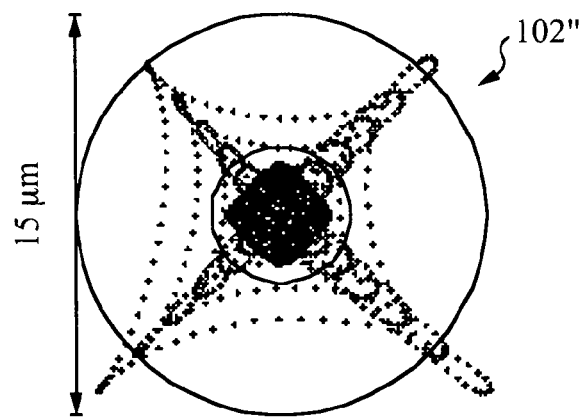

FIGS. 5A-B are spot diagrams illustrating the images of the broadband source after first and second toroidal mirrors that are donut-shaped instead of barrel-shaped.

Figure 6:
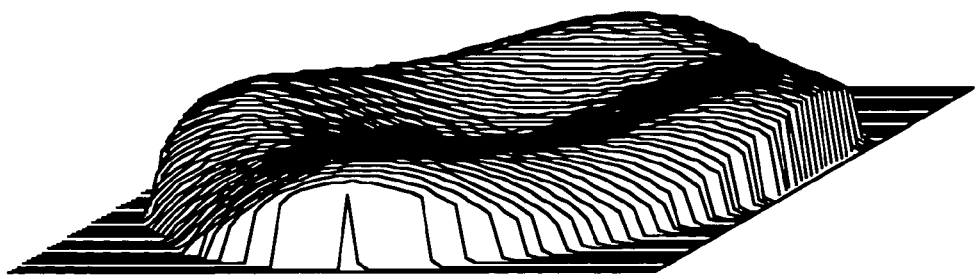

FIG. 6 is a wave front diagram at the spot when using donut-shaped toroidal mirrors.

FIGS. 7A-B are spot diagrams of source images after the first and second toroidal mirrors that are a crossed combination of donut and barrel-shaped mirrors.

FIG. 8 is a wave front diagram at the spot when using the crossed combination of donut and barrel-shaped toroidal mirrors.

FIGS. 9A-B are spot diagrams of source images after the first and second toroidal mirrors that are a crossed combination of barrel and donut-shaped mirrors.

Figure 10:
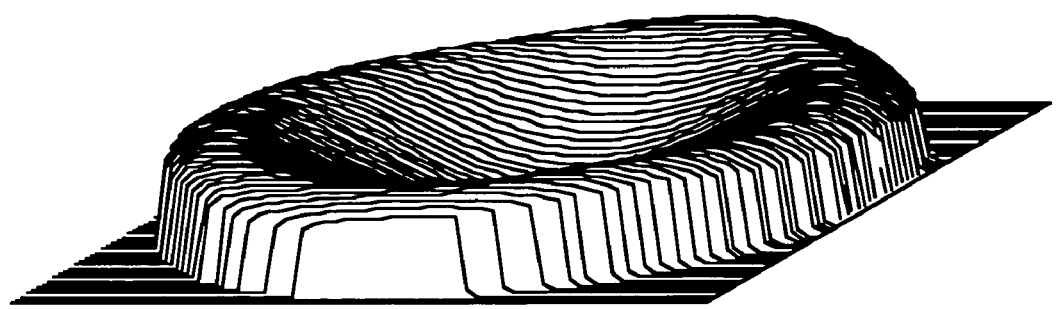

FIG. 10 is a wave front diagram at the spot when using the crossed combination of barrel and donut-shaped toroidal mirrors.

Figure 11:
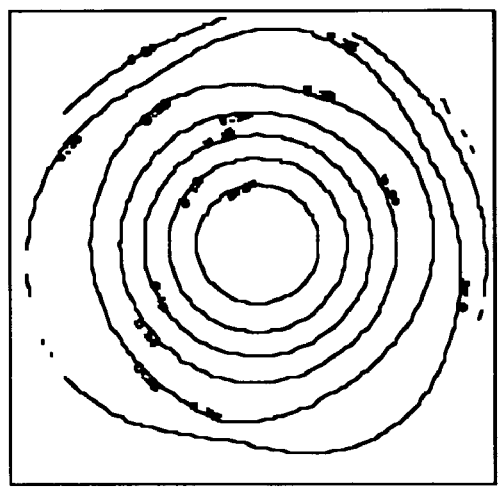

FIG. 11 is a wave front function corresponding to the wave front diagram of FIG. 10

Figure 12:
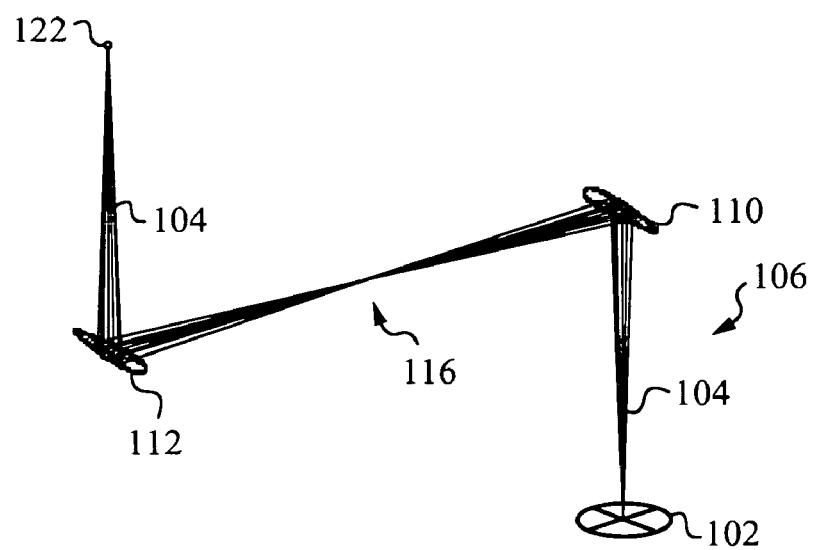

FIG. 12 is a ray trace diagram illustrating an alternative arrangement of two parallel toroidal mirrors.

Figure 13:
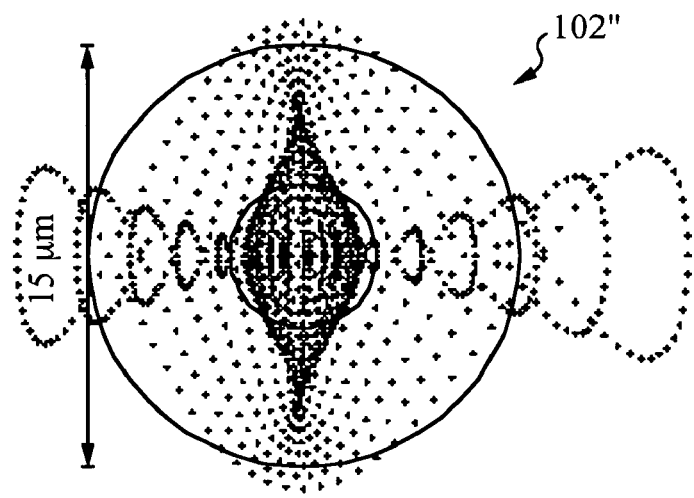

FIG. 13 is a spot diagram of the source at the second focal point after the second mirror.

Figure 14:
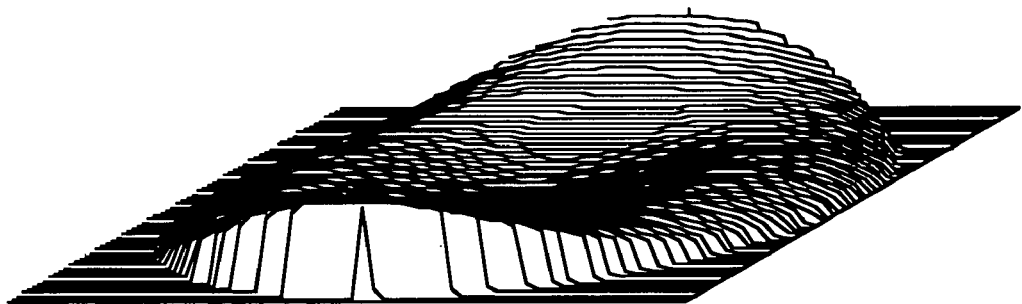

FIG. 14 is a wave front diagram at the second spot for the parallel arrangement of FIG. 12.

Figure 15:
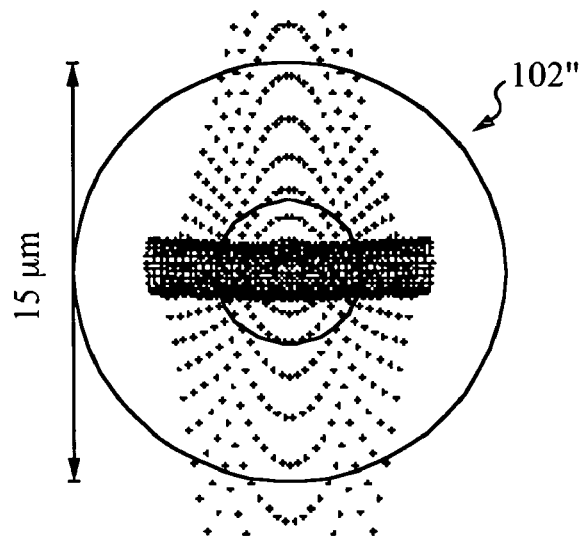

FIG. 15 is a spot diagram of the source at the second focal point after the second mirror for the case where both mirrors are barrel-shaped and parallel.

Figure 16:
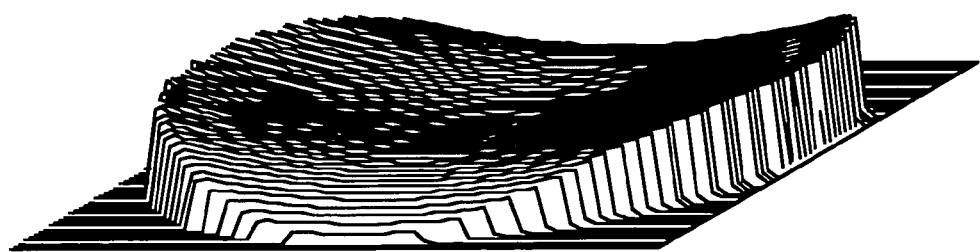

FIG. 16 is a wave front diagram at the second focal point for the case of two parallel barrel-shaped mirrors.

Figure 17:
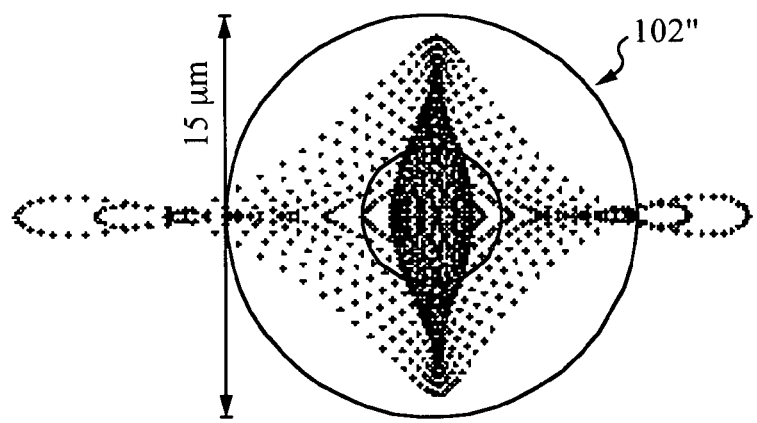

FIG. 17 is a spot diagram of the source at the second focal point after the second mirror for the case where the mirrors are barrel and donut-shaped and parallel aligned.

Figure 18:
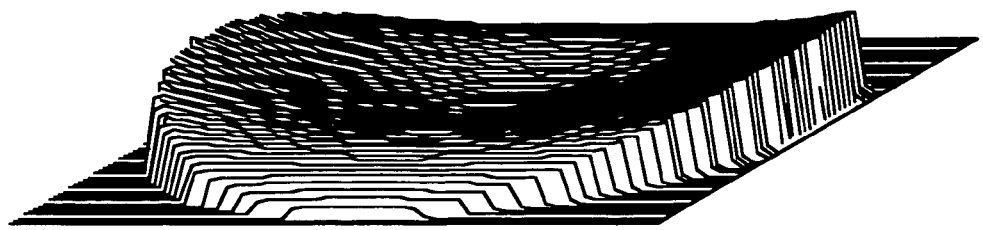

FIG. 18 is a wave front diagram at the second focal point for the case of parallel aligned barrel and donut-shaped mirrors.

Figure 19:
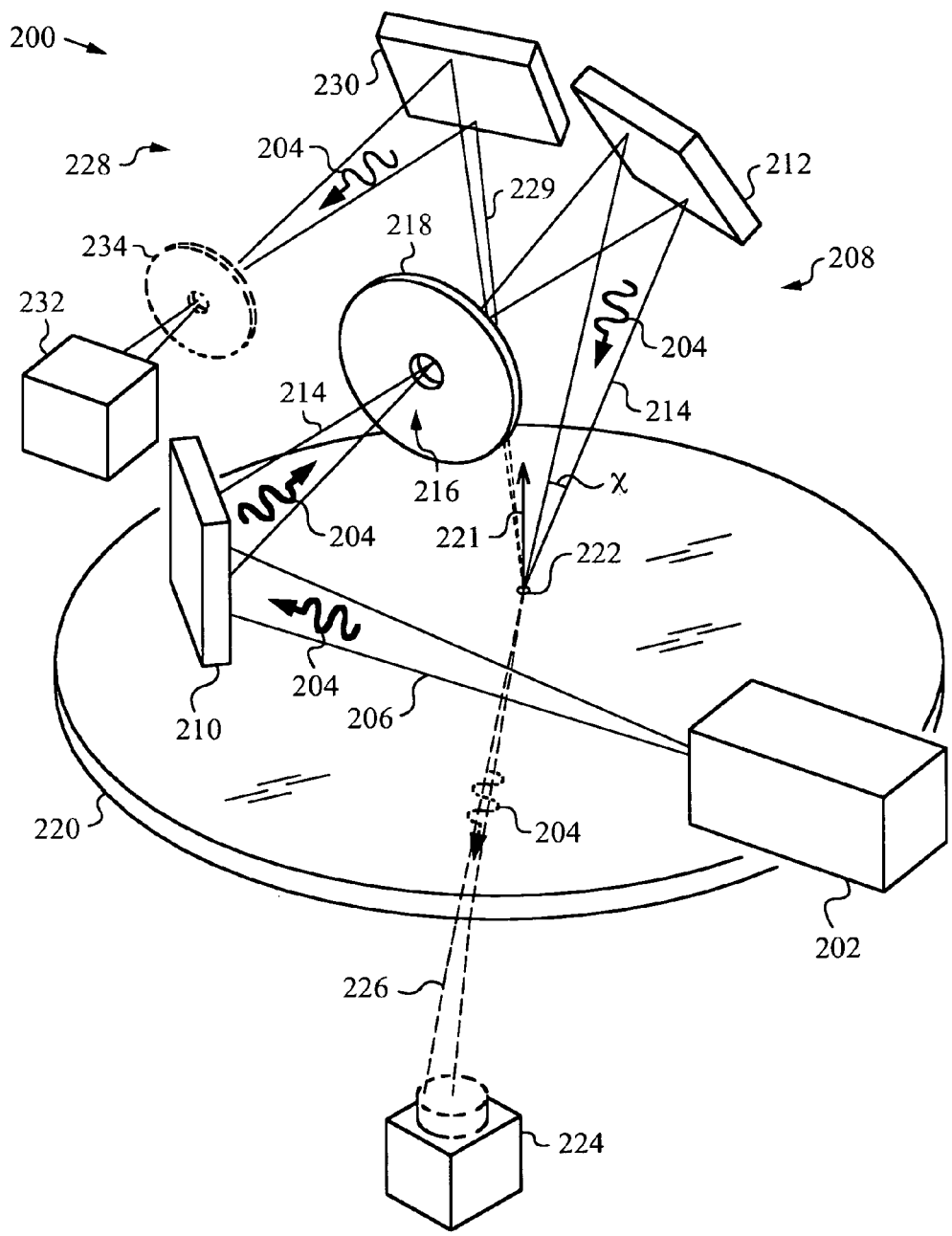

FIG. 19 is an isometric view of another apparatus for optical metrology in accordance with the invention.

Figure 20:
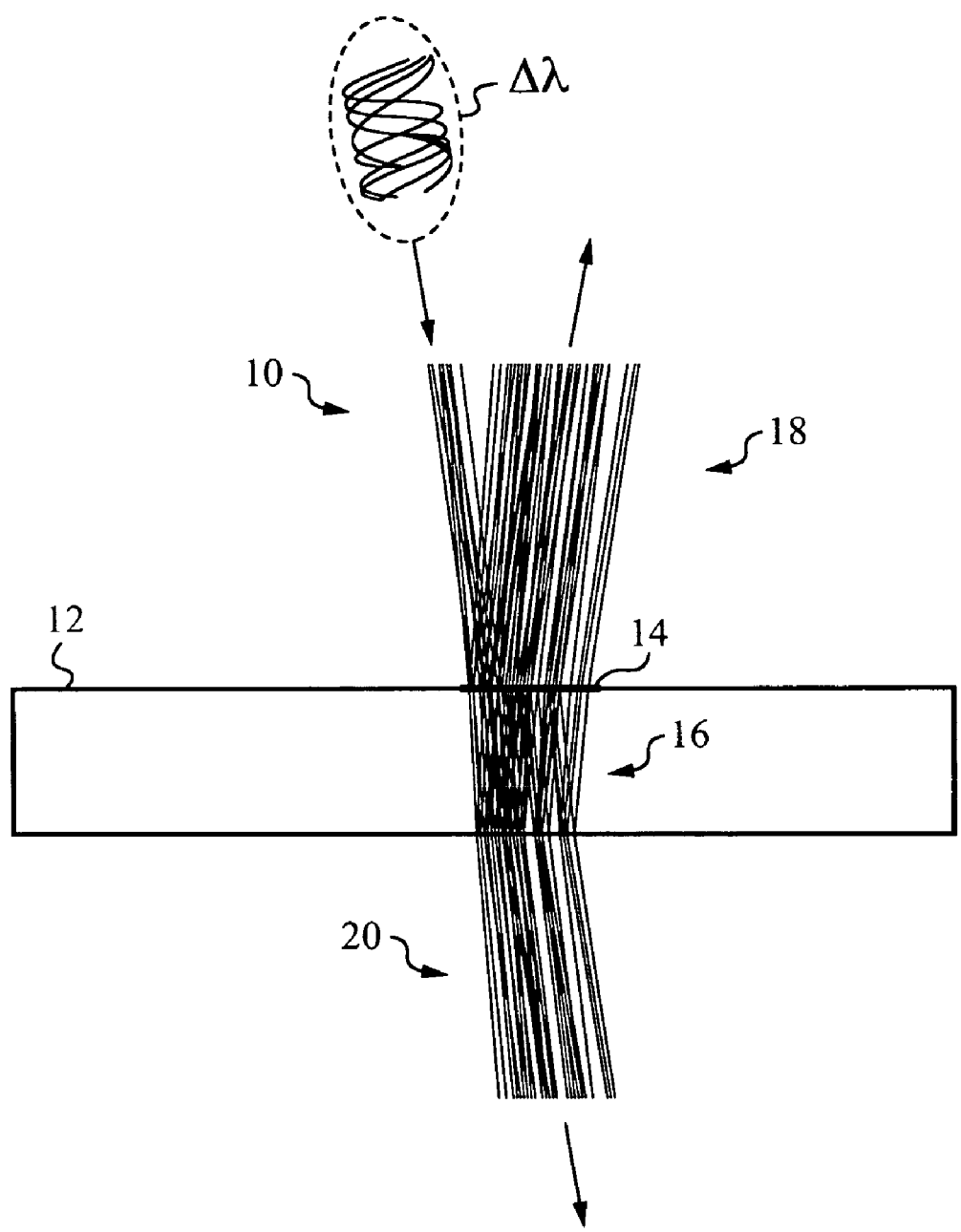

FIG. 20 (Prior Art) is an optical ray trace of broadband radiation incident on a semitransparent sample studied in a typical optical system.

Figure 21:
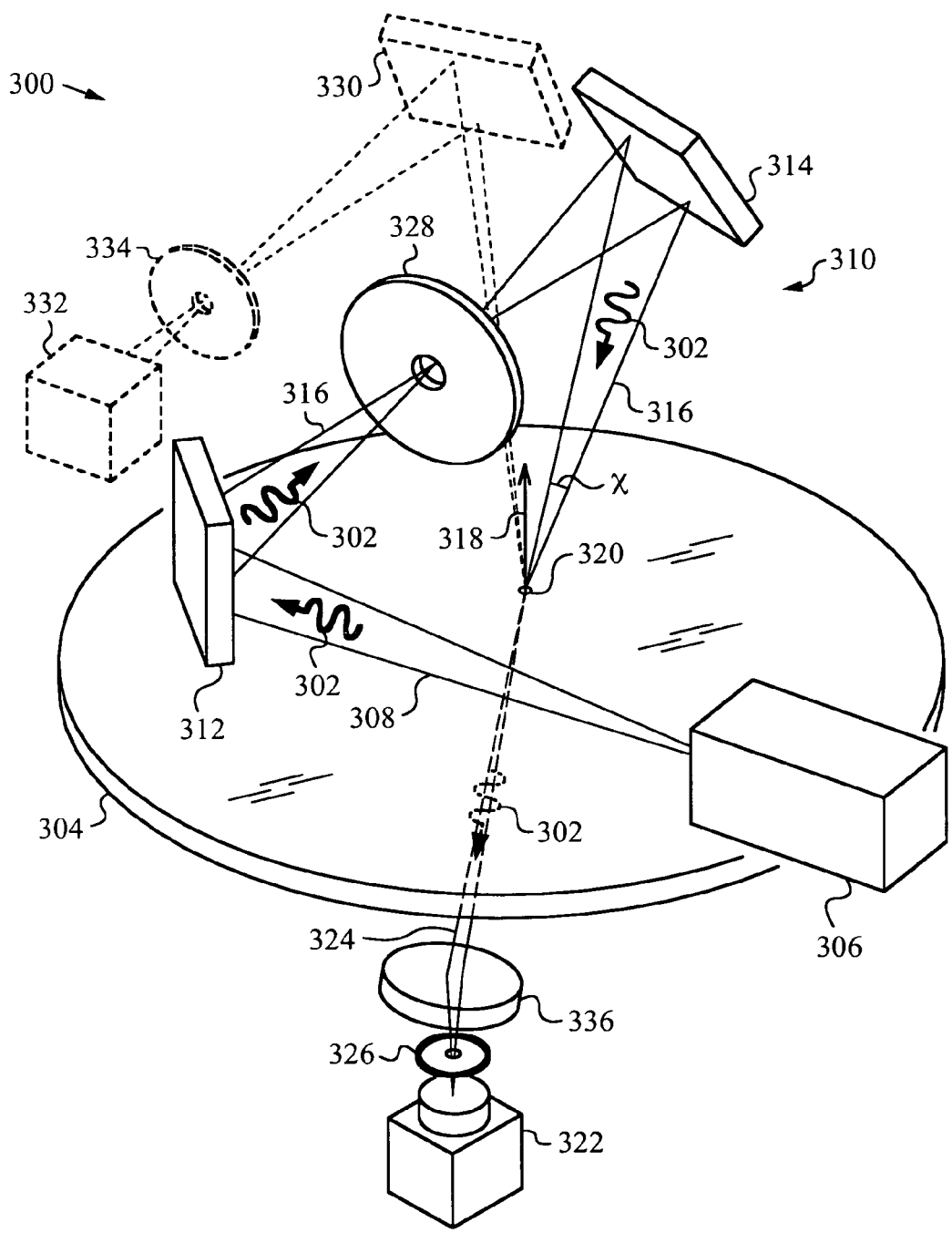

FIG. 21 is an isometric view of an exemplary apparatus in accordance with the invention.

Figure 22A:
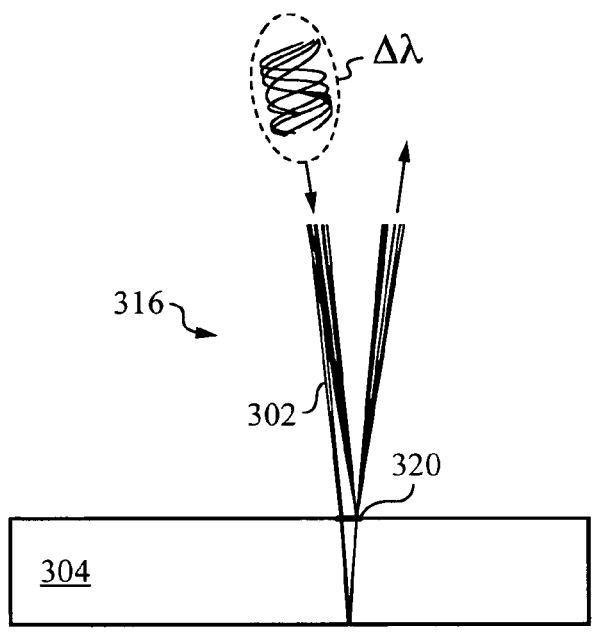
Figure 22B:
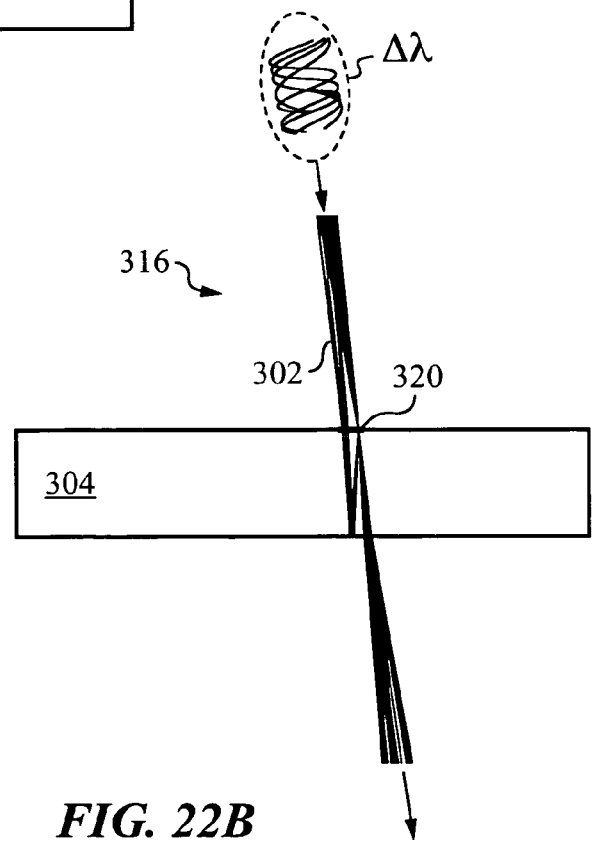

FIGS. 22A-B are optical ray traces illustrating the effects of entrance aperture on reflected and transmitted radiation.

FIGS. 23A-C are optical ray traces illustrating the effects of sampling aperture and entrance aperture on reflected and transmitted radiation.

Figure 24A:
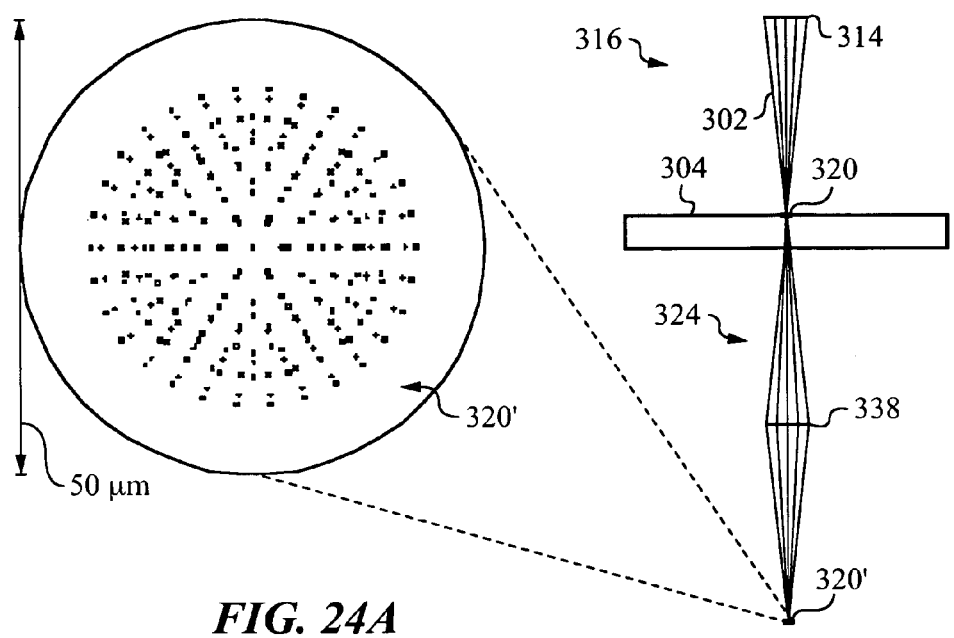
Figure 24B:
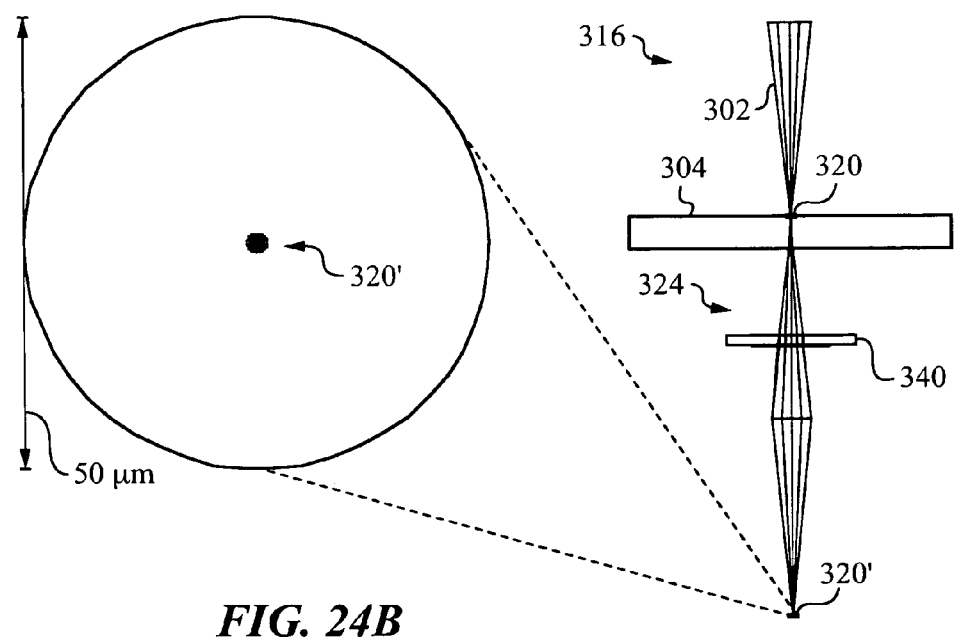

FIGS. 24A-B are diagrams illustrating chromatic dispersion compensation in a broadband test beam at normal incidence.

FIGS. 25A-F are diagrams illustrating chromatic dispersion compensation in a broadband test beam at off-normal incidence in accordance with the invention.

Figure 26:
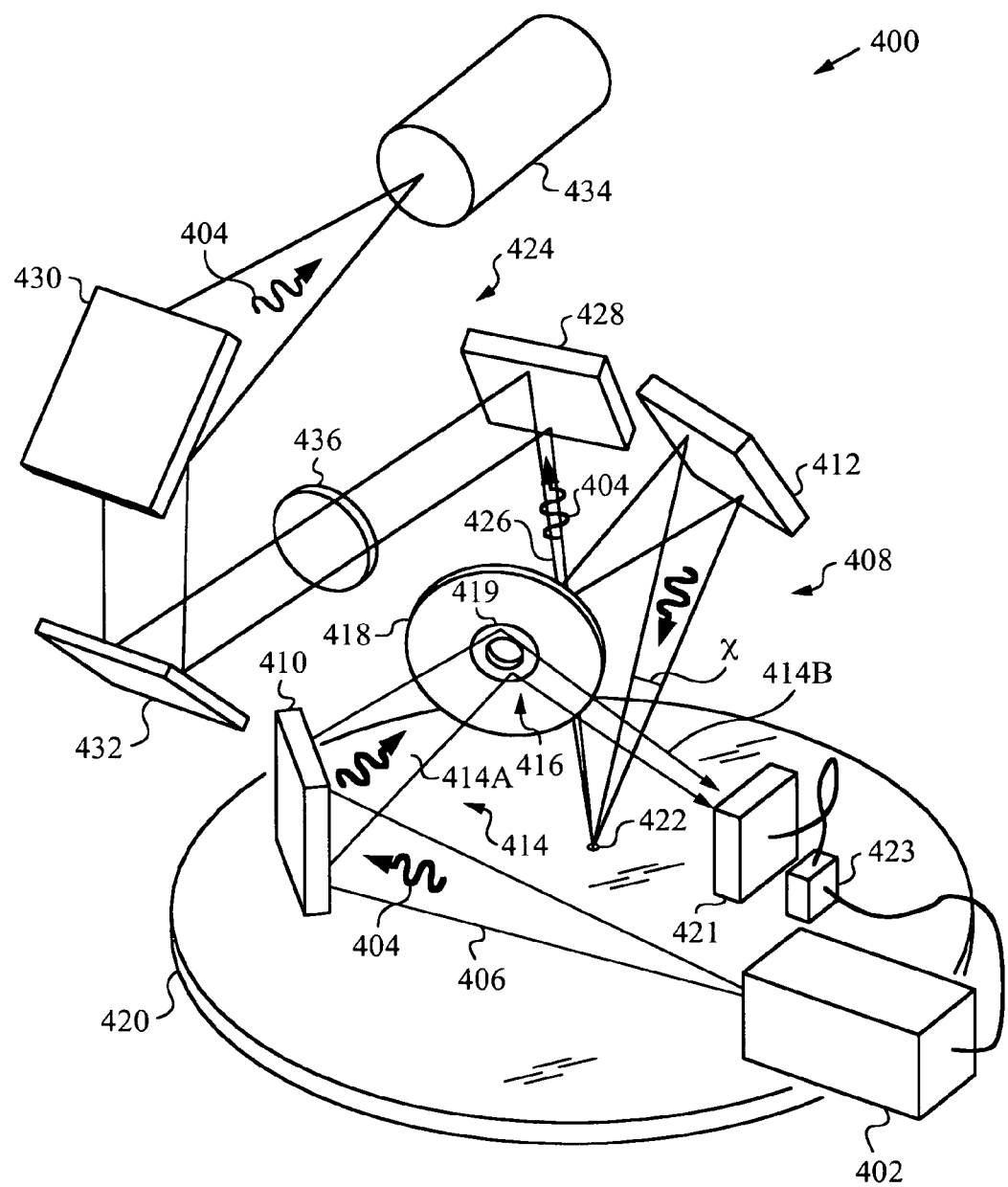

FIG. 26 is a three-dimensional diagram illustrating an apparatus employing broadband test beam monitoring in accordance with the principles of invention.

Figure 27:
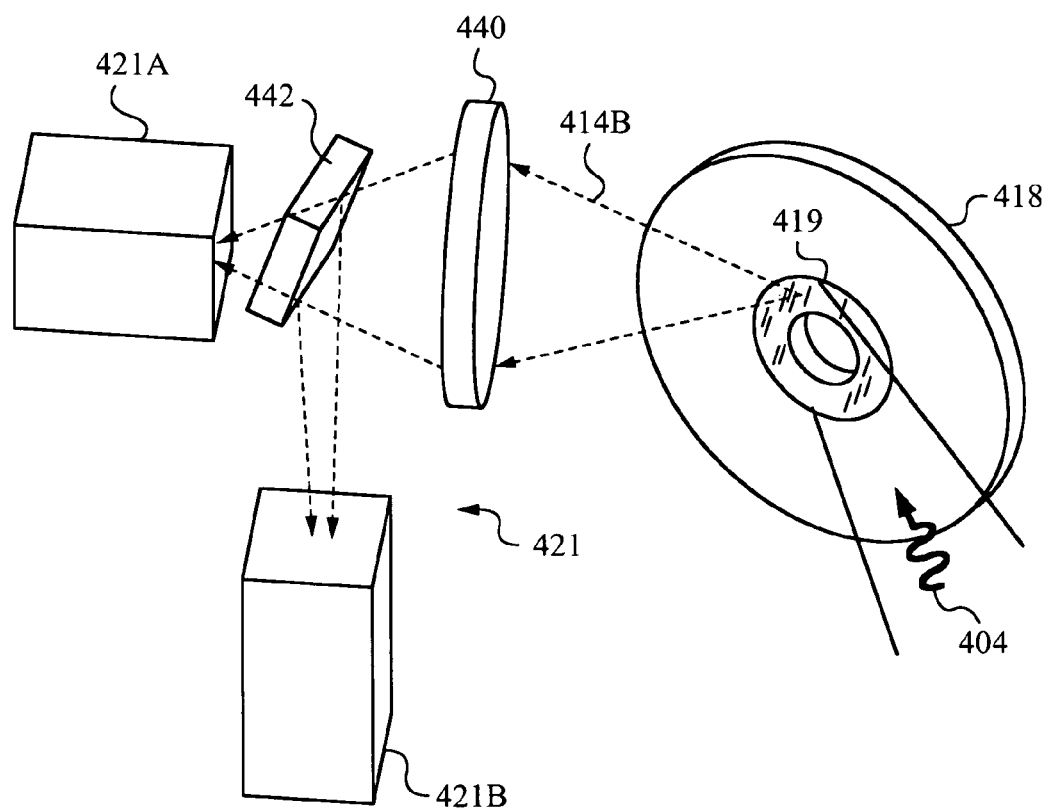

FIG. 27 is a three-dimensional diagram of a sampling aperture employed in combination with an imaging optic for imaging the reflective region surrounding the aperture.

Figure 28:
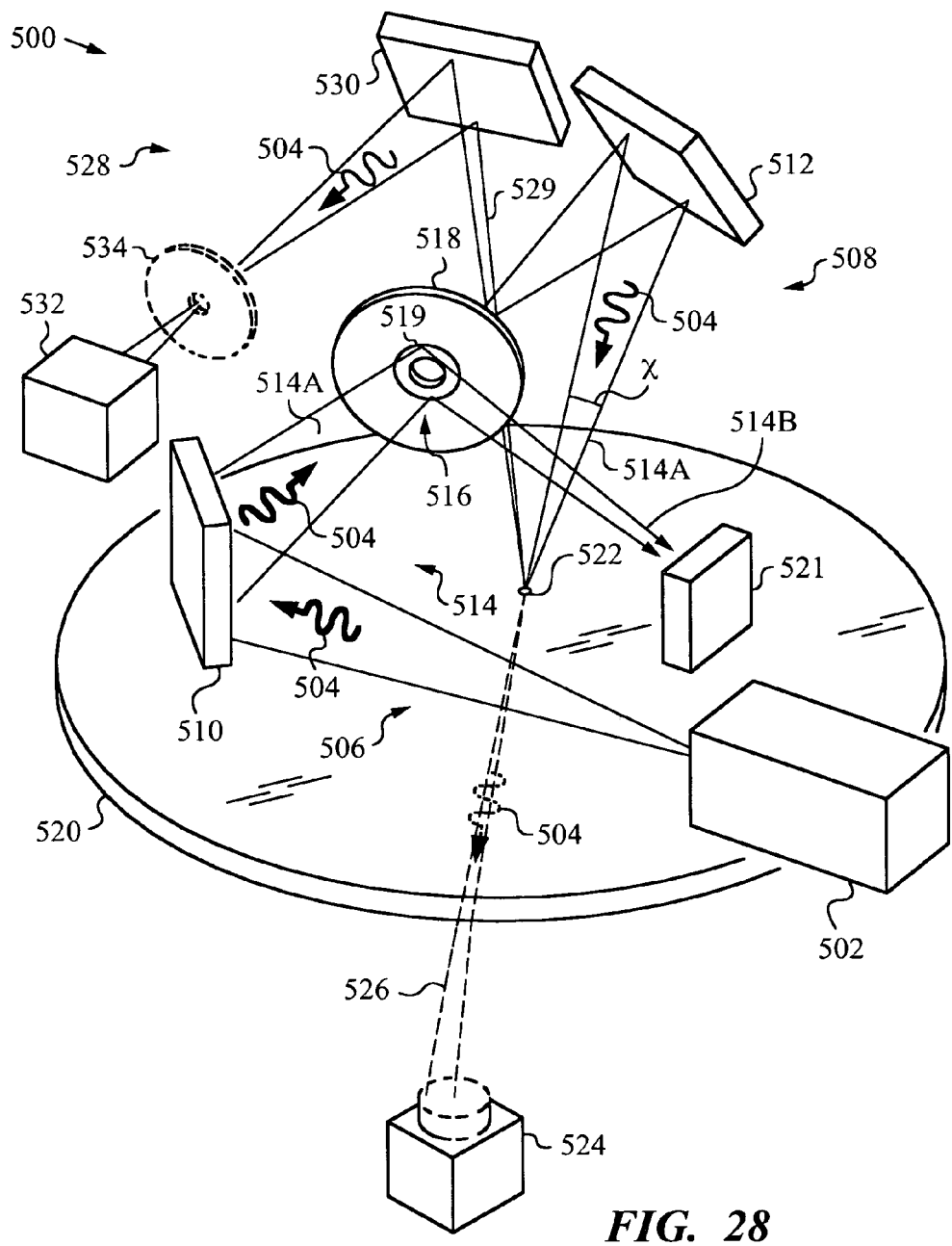

FIG. 28 is a three-dimensional view of another apparatus in accordance with the invention.

Figure 29:
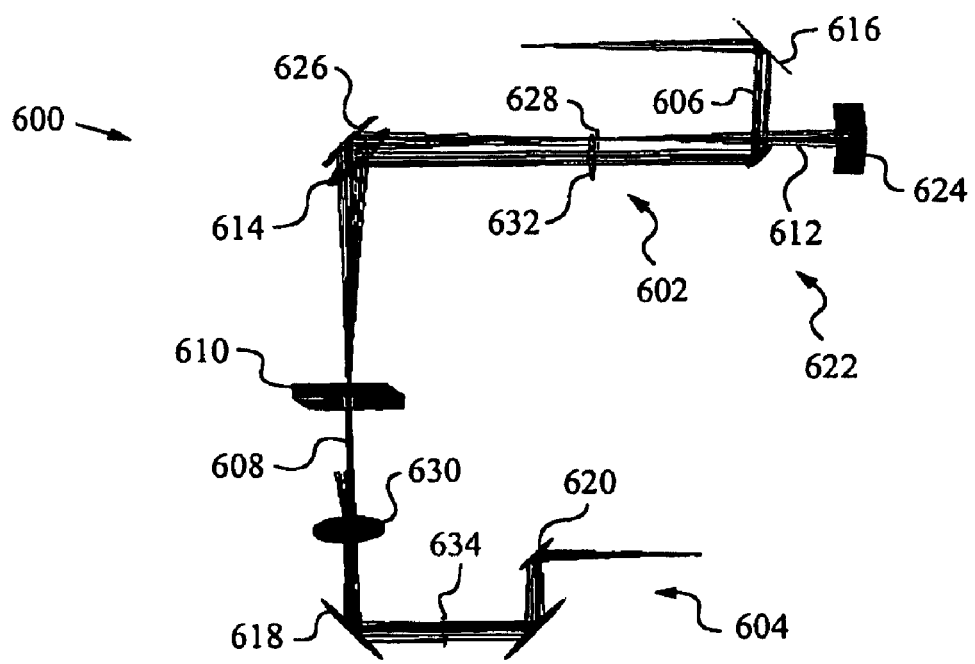

FIG. 29 is a three-dimensional ray trace diagram of an alternative apparatus in accordance with the invention for performing reflectance and transmittance measurements.

Figure 30:
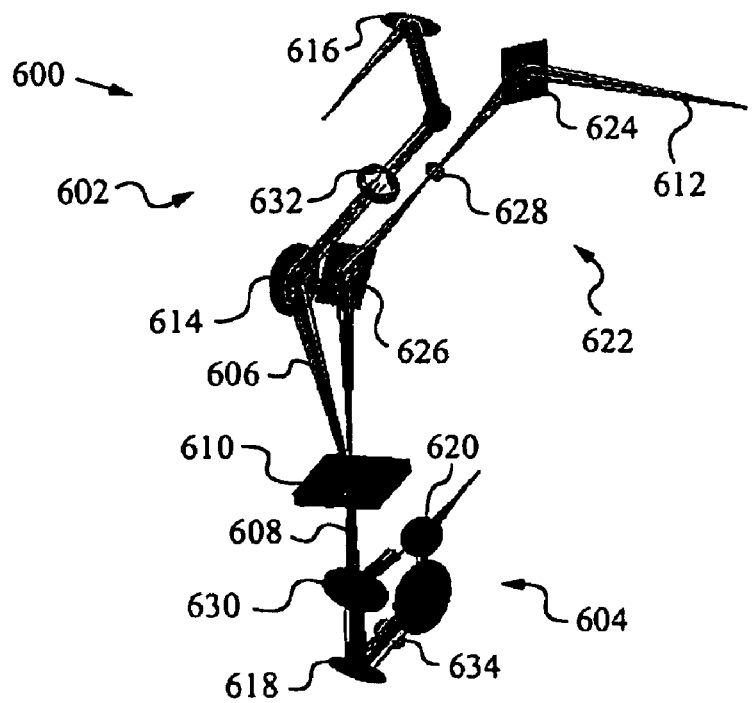

FIG. 30 is a three-dimensional ray trace diagram of the alternative apparatus of FIG. 29 from a different point of view.

DETAILED DESCRIPTION

Figure 1:
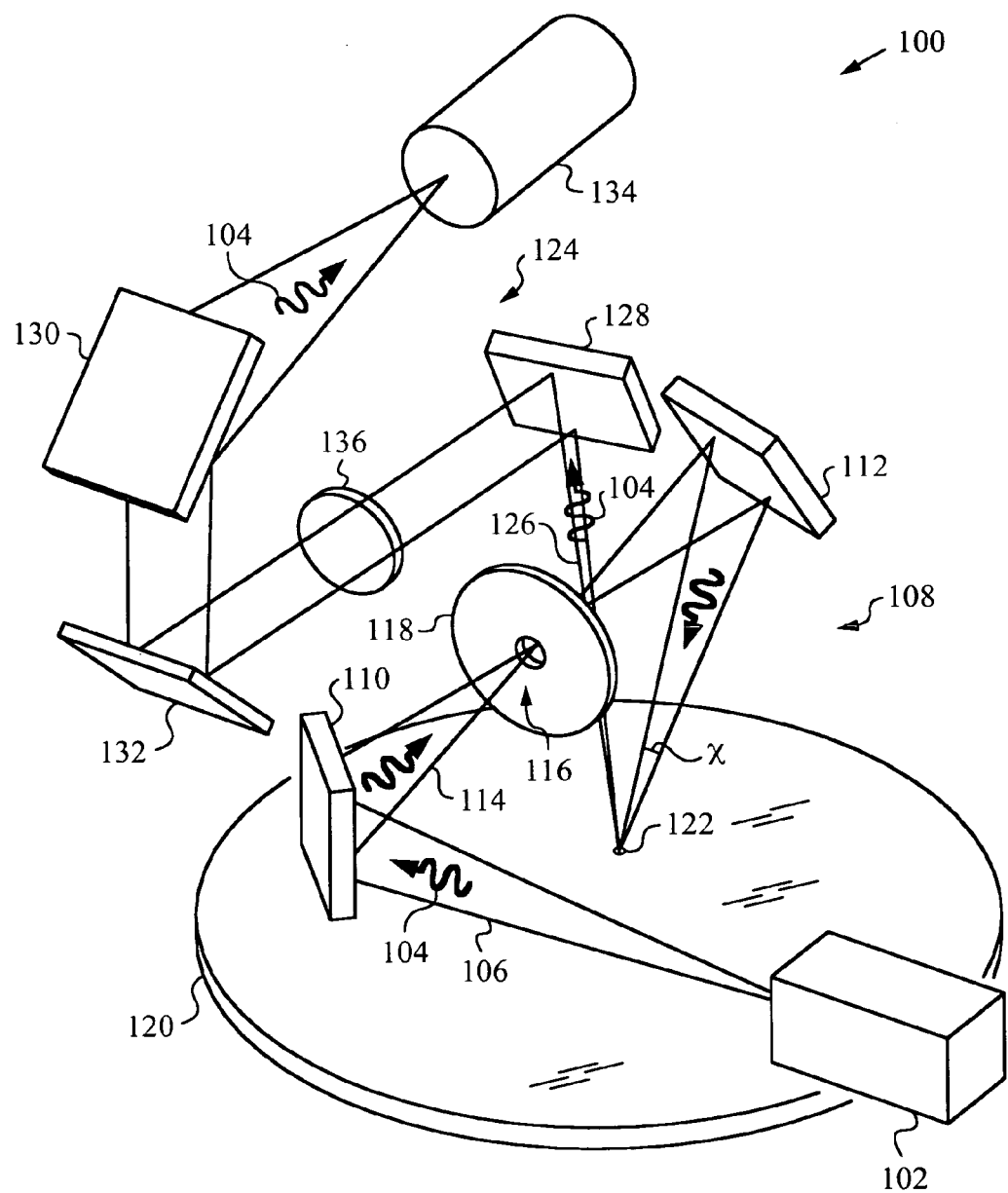
FIG. 1 is an isometric view of an apparatus for optical metrology in accordance with the invention.

The isometric view in FIG. 1 illustrates an apparatus 100 for performing optical reflectance metrology in accordance with the principles of the invention. Apparatus 100 has a broadband source 102 for providing broadband radiation 104 spanning a wide spectrum or wavelength range $\Delta\lambda$. Wavelength range $\Delta\lambda$ may extend from the deep ultra-violet (DUV), e.g., 190 nm or less, to the far infra-red (IR), e.g., 3,000 nm or more. The type of metrology to be practiced will determine the exact width of wavelength range $\Delta\lambda$. Source 102 can be a compound source that uses two or more individual sources to emit broadband radiation 104 in sub-bands spanning wavelength range $\Delta\lambda$. For example, a visible sub-band of radiation 104 can be generated by a lamp, such as a halogen lamp or a discharge lamp, and an ultra-violet sub-band of radiation 104 can be produced by a DUV deuterium lamp. Additional sources can be used to span the far infra-red part of wavelength range $\Delta\lambda$, as desired. In some embodiments, the broad wavelength range $\Delta\lambda$ may extend from 190 nm up to 3,000 nm and beyond. Compound broadband sources are particularly efficient when the metrology method requires emission of stable levels of radiation 104 over a very wide wavelength range $\Delta\lambda$ since the sources can be individually adjusted.

Radiation 104 is emitted in an output beam 106 toward a first reflective optics 108. Preferably, the output beam 106 has a Gaussian beam profile or, in other words, the cross-section of output beam 106 is Gaussian.

In the present embodiment, optics 108 have a pair of curved mirrors, namely a first toroidal mirror 110 and a second toroidal mirror 112. Various arrangements of toroidal mirrors 110, 112 are possible including a crossed arrangement, which is employed in this embodiment. Mirrors 110, 112 are set up to intercept radiation 104 and shape it into a broadband test beam 114. In addition, since mirrors 110, 112 are crossed they cause test beam 114 to converge and produce an image of source 102 in an image plane at a beam waist 116.

A sampling aperture 118 for filtering broadband test beam 114 is positioned in the image plane or at waist 116 between toroidal mirrors 110, 112. The size of aperture 118 is chosen so that a center portion of test beam 114 is filtered or passed through aperture 118. When test beam 114 has a Gaussian cross-section, as in the preferred embodiment, the center portion should contain at most 67% of the total intensity of test beam 114. In other words, the filtered center portion of beam 114 corresponds to radiation contained within the full width half maximum (FWHM) region or a single deviation from the maximum at beam center or less.

Broadband test beam 114 is guided by optics 108 so that it impinges on a sample 120. In the present embodiment, sample 120 is a patterned semiconductor wafer, i.e., sample 120 is a silicon wafer bearing miniature features (not explicitly shown). Of course, it will be appreciated by a person skilled in the art that sample 120 can be any bulk sample of material that is reflective or at least semi-reflective over broad spectrum or wavelength range Δλ provided by broadband source 102 and that it may or may not bear miniature features.

Optics 108 guide test beam 114 such that it is incident on sample 120 at a spot 122. Optics 108 also dictate the extent of a cone angle χ of test beam 114 incident on sample 120. The size of spot 122 is kept small in the present application, e.g., on the order of 50 μm or less. It will be appreciated, however, that the size of spot 122 can vary and that in some metrology applications it is preferable to have a large spot, e.g., on the order of several hundred μm. For example, when the miniature features of sample 120 form a grating it is preferable to use large spot 122 in conjunction with small cone angle χ, e.g., less than 3 degrees and more preferably on the order of a degree or less. On the other hand, when sample 120 has no miniature features to examine (e.g., sample 120 is a film) it is preferable to use very small spot 122, e.g., 30 and a large cone angle χ, e.g., on the order of 5-7 degrees.

A second reflective optics 124 is provided for shaping a reflected response beam 126 constituted by broadband radiation 104 that is reflected from sample 120 at spot 122. Second reflective optics 124 uses curved mirrors 128, 130 and a flat folding mirror 132 to deliver response beam 126 to a first detector 134 for examination. Preferably, mirrors 128, 130 are two symmetrically placed parabolic mirrors that are off-axis such that they image spot 122 to first detector 134. Alternatively, mirrors 128, 130 are two parallel toroidal mirrors. An optional polarizer 136 is provided in the collimated portion of the beam path of response beam 126 for performing polarization-dependent measurements.

The operation of apparatus 100 and more specifically the wave front distortion in the test beam 114 depends on the actual type or shape of the toroidal mirrors 110, 112 chosen in first reflective optics 108. Specifically, it is important to examine in more detail how toroidal mirror 110 focuses test beam 114 at beam waist 116 and how torroidal mirror 112 collects diverging test beam 114 and focuses it at spot 122 on sample 120.

Figure 2:
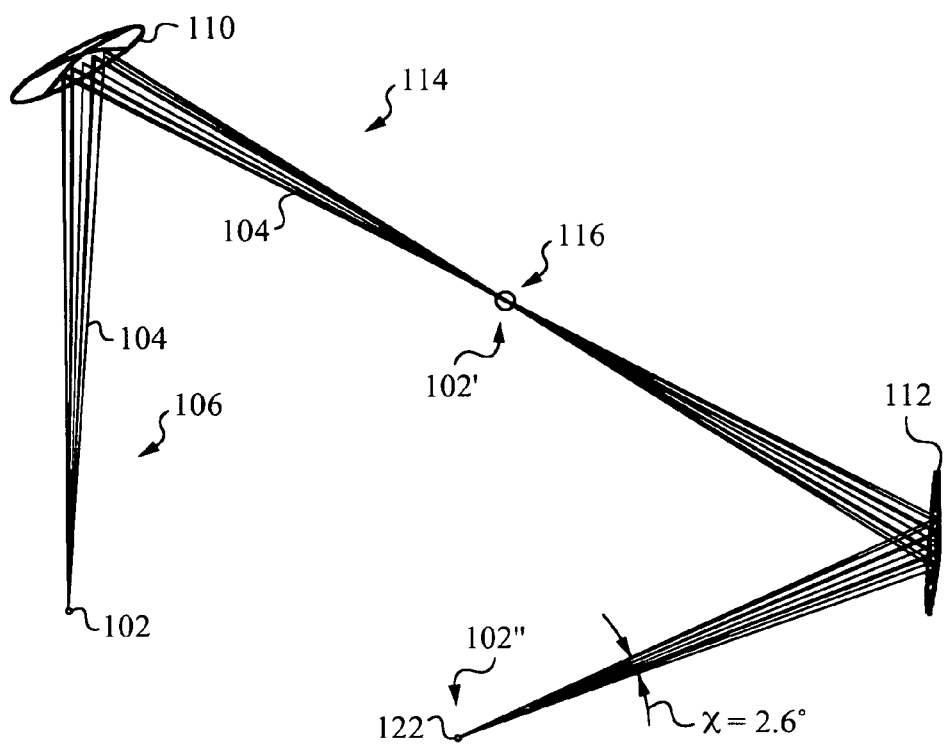
FIG. 2 is a ray trace diagram illustrating the operation of the two crossed toroidal mirrors.

FIG. 2 illustrates the path of beams 106 and 114 of radiation 104 for crossed toroidal mirrors 110, 112 in more detail with a ray trace diagram. Source 102 is a point source in this ray trace. The half cone angle χ in this example is 2.6 degrees. In general, and for the purpose of the present description, toroidal surfaces are formed by defining a curve in the Y-Z plane, and then rotating this curve about an axis parallel to the Y axis and intersecting the Z axis (where the Z axis is defined to be perpendicular to the mirror surface). The two radii are used to define the toroid. The curvature in the Y-Z plane is defined as a base radius (R1). This curve is then rotated about an axis a distance R from the vertex and this distance R is referred to as the radius of rotation (R2, also called the radius of the cylinder curve). When the rotation radius is longer than the radius of the base (R2>R1), the mirror is called a donut-type toroid, otherwise (R1>R2) and the mirror is called a barrel-shaped toroid.

In the first example, crossed toroidal mirrors 110, 112 are barrel-shaped with radii R1, R2 equal to 75 mm and 150 mm respectively. The arrangement of crossed barrel-shaped toroidal mirrors 110, 112 generates two images of source 102. Specifically, a first image 102' of source 102 is found after mirror 110. Image 102' at the location of beam waist 116 is illustrated in the spot diagram of FIG. 3A. The spot is 15 μm in diameter, the airy radius is 2.554 μm and the rms radius is 2.332 μm. A second image 102" of source 102 is found after mirror 112. Image 102" at the location of spot 122 is shown in the spot diagram of FIG. 3B. Once again, the spot is 15 μm in diameter, the airy radius is 22.541 μm and the rms radius is 31.154 μm.

One of the main advantages of employing crossed toroidal mirrors 110, 112 in first reflective optics 108 is the high uniformity of the wave front achieved at spot 122 on sample 120. FIG. 4 illustrates a wave front diagram at second image 102" or at spot 122. The maximum peak-to-valley distance is at about 0.45 waves and the rms deviation is approximately 0.1 waves at a reference wavelength of 190 nm.

In an alternative embodiment of first reflective optics 108, crossed toroidal mirrors 110, 112 are donut-shaped instead of barrel-shaped. FIGS. 5A-B are spot diagrams of images 102' and 102" of broadband source 102 after first and second donut-shaped toroidal mirrors 110, 112 at beam waist 116 and at spot 122, respectively. In FIG. 5A the spot is 15 μm in diameter, the airy radius is 2.554 μm and the rms radius is 2.629 μm. In FIG. 5B the spot is also 15 μm in diameter, the airy radius is 2.554 μm and the rms radius is 3.185 μm. FIG. 6 is a wave front diagram at second image 102" and indicates that the maximum is about 0.42 waves with an rms deviation of about 0.07 waves at a reference wavelength of 190 nm.

A crossed combination of toroidal mirrors 110, 112 also permits for combinations of shape types. In other words, one of mirrors 110, 112 can be donut-shaped and the other barrel-shaped. FIGS. 7A-B illustrate spots 102', 102" for the case where mirror 110 is donut-shaped and mirror 112 is barrel-shaped. Both spots as shown in the diagrams are 15 μm in diameter, with both airy disc radii being 2.553 μm and rms radii being 2.678 μm and 1.816 μm respectively. FIG. 8 is the corresponding wave front diagram at spot 122 or at the second focal point. In this case the maximum is about 0.28 waves and the rms deviation is about 0.07 waves at 190 nm.

The imaging quality of a crossed combination of barrel-shaped toroidal mirror 110 and donut-shaped toroidal mirror 112 is shown in FIGS. 9A-B. These spot diagrams are both 15 μm in diameter with equal airy disc radii of 2.553 μm and rms radii of 2.363 μm and 1.833 μm. The corresponding wave front diagram shown in FIG. 10 confirms that the maximum is again about 0.28 waves with an rms deviation of about 0.07 waves at 190 nm. A wave front function shown in FIG. 11 illustrates the corresponding isometrics of the wave fronts shown in the diagram of FIG. 10.

In another embodiment of apparatus 100, first reflective optics 108 take advantage of toroidal mirrors 110, 112 that are arranged in parallel, as illustrated by the ray trace diagram of FIG. 12. Once again, toroidal mirrors 110, 112 themselves can be either donut-shaped or barrel-shaped. The radii of toroidal mirrors 110, 112 are 75 mm and 150 mm, as before, and half cone angle χ is 2.6 degrees.

In a first example of a parallel arrangement, mirrors 110, 112 are both donut-shaped. The corresponding spot diagram of the second image spot 102" after second mirror 112 at the focal point or at spot 122 is shown in FIG. 13. The spot diameter is 15 μm, the airy disc radius is 2.557 μm and the rms radius is 4.978 μm. FIG. 14 shows the corresponding wave front diagram at reference wavelength of 190 nm at which the maximum peak-to-valley distance is about 1.22 waves and the rms deviation is about 0.21 waves.

FIG. 15 shows the second spot 102" in the case where mirrors 110, 112 are both barrel-shaped and parallel. The spot diameter is 15 μm, the airy disc radius is 2.56 μm and the rms radius is 4.641 μm. Corresponding wave front diagram shown in FIG. 16 indicates a maximum peak-to-valley distance of about 1.11 waves and an rms deviation of about 0.19 waves at 190 nm. The corresponding case of parallel-aligned barrel and donut-shaped mirrors 110, 112 is shown in the spot diagram of FIG. 17 and the wave front diagram of FIG. 18. For this case the spot diameter is 15 µm, the airy disc radius is 2.558 µm, the rms radius is 4.603 µm, the maximum peak-to-valley is about 1.19 waves and the rms deviation is about 0.2 waves for radiation 104 at 190 nm.

A person skilled in the art will recognize that the various arrangements and combinations of toroidal mirrors 110, 112 that are possible can be selected based on the requirements and trade-offs of the metrology method and type of sample 120. In general, apparatus 100 will be most advantageous in optical metrology situations where spot 122 needs to have a very uniform wave front. The size and placement of sampling aperture 118 at waist 116 in the image plane between toroidal mirrors 110, 112, whether in the crossed or parallel arrangement, will further aid in achieving a uniform spot 122 through spatial filtering.

Returning now to FIG. 1, reflected beam 126 is shaped by second reflective optics 124. In addition, second reflective optics 124 uses curved mirrors 128, 130 and a flat folding mirror 132 to deliver response beam 126 to a detector 134 for examination. When mirrors 128, 130 are two symmetrically placed parabolic mirrors that are off-axis they perform particularly well at imaging spot 122 to detector 134. In this case, the low distortion of the wave front at spot 122 is preserved at detector 134. Optional polarizer 136 provided in the collimated portion of the beam path of response beam 126 can be used for performing polarization-dependent measurements on sample 120.

An apparatus in which the response beam includes a reflected beam is also useful for examining samples that are partially or semi-transparent. FIG. 19 illustrates in an isometric view an apparatus 200 that can be used to study a sample 220 that is semi-transparent. Apparatus 200 has a broadband source 202 for providing broadband radiation 204 spanning a broad wavelength range $\Delta\lambda$. Sample 220 may be partly transparent over entire wavelength range $\Delta\lambda$ or just a portion thereof.

Radiation 204 is emitted in an output beam 206 toward a first reflective optics 208. Preferably, output beam 206 has a Gaussian beam cross-section. Optics 208 employ a pair of toroidal mirrors 210, 212 for forming a broadband test beam 214 from output beam 206. As discussed above, toroidal mirrors 210, 212 can be barrel or donut-shaped and they can be positioned in a crossed or parallel arrangement. In any of these arrangements, mirrors 210, 212 cause test beam 214 to converge and produce an image of source 202 in an image plane at a beam waist 216.

A sampling aperture 218 for filtering broadband test beam 214 is positioned in the image plane or at waist 216 between toroidal mirrors 210, 212. The size of aperture 218 is chosen so that a center portion of test beam 214 is filtered or passed through aperture 218. When test beam 214 has a Gaussian cross-section, as in the preferred embodiment, the center portion should contain at most 67% of the total intensity of test beam 214.

Test beam 214 is guided by optics 208 so that it impinges on a semi-transparent sample 220 at a spot 222. Depending on the metrology method and type of sample 220, mirrors 210, 212 are chosen to define a suitable cone angle $\chi$ of test beam 214 and size of spot 222. In the present embodiment, the size of spot 222 is kept on the order of 50 µm or less. The angle of incidence of test beam 214 is preferably steep with respect to a surface normal 221, such that test beam 214 is incident slightly off-normal at a spot 222 on sample 220.

Apparatus 200 has a second detector 224 positioned below sample 220 for registering or detecting a transmitted response beam 226 of broadband radiation 204 that is transmitted through sample 220. More precisely, second detector 224 is sensitive over a spectral range corresponding to wavelength range $\Delta\lambda$ such that it can detect broadband radiation 204 that passes through sample 220.

A second reflective optics 228 is provided for shaping a reflected response beam 229 constituted by broadband radiation 204 that is reflected from sample 220 at spot 222. Second reflective optics 228 uses a single curved mirror 230 to deliver response beam 229 to a detector 232 for examination. Preferably, mirror 230 is a curved mirror that images spot 222 to detector 232. An optional entrance aperture 236 is provided in the beam path of response beam 229 for performing additional spatial filtering.

In addition to excellent wave front properties, the apparatus of the present invention can be employed for compensating a chromatic dispersion that is produced in broadband radiation that is transmitted through the sample in transmittance measurements. To better understand the principles of chromatic dispersion compensation it is instructive to first review the optical ray trace of FIG. 20. The diagram shows broadband radiation 10 covering a spectrum or wavelength range $\Delta\lambda$ incident on a semi-transparent sample 12 in a typical prior art optical system (not shown). Since wavelength range $\Delta\lambda$ in typical scatterometric applications is broad, e.g., from the ultra-violet into the infra-red, a certain amount of chromatic dispersion is apparent at a point of incidence 14. The chromatic dispersion is due to aberrations in the optical system. Furthermore, the multiple internal reflections 16 within sample 12 cause additional chromatic dispersion due to multiple reflected and transmitted orders 18, 20. The accumulated total chromatic dispersion makes it virtually impossible for a detector of the optical system to obtain a high-quality and tightly focused response beam of either transmitted or reflected radiation 10.

FIG. 21 is an isometric view of an apparatus 300 in accordance with the invention for compensating chromatic dispersion that is produced in a broadband radiation 302 after it is transmitted through a sample 304. Apparatus 300 has a broadband source 306 that is preferably compound and uses two or more individual sources to emit broadband radiation 302 in sub-bands covering wavelength range $\Delta\lambda$. For example, a visible sub-band of radiation 302 is generated by a lamp, such as a halogen lamp or a discharge lamp, and an ultra-violet sub-band of radiation 302 is produced by a DUV deuterium lamp. Additional sources can be used to span the far infra-red spectral region, as desired. In some embodiments, the wavelength range $\Delta\lambda$ may extend from 190 nm up to 3,000 nm and beyond.

Preferably, whether compound or not, source 306 provides broadband radiation 302 in the form of a beam 308 that is Gaussian and can be easily shaped and directed by the optics of apparatus 300. Apparatus 300 has a first reflective optics 310 for guiding and shaping beam 308 of broadband radiation 102.

First reflective optics 110 is made up of two curved mirrors 312, 314 that are toroidal. They shape beam 308 of broadband radiation 302 into a broadband test beam 316. Furthermore, mirror 314 directs test beam 316 at sample 304 at a certain angle of incidence. A person skilled in the art will recognize that other curved mirrors, such as parabolic mirrors, can be used in the construction of reflective optics 310.

The angle of incidence is steep with respect to a surface normal 318, such that test beam 316 is incident a few degrees off-normal at a spot 320 on sample 304. The size of spot 320 and cone angle $\chi$ of test beam 316 should be adjusted depending on type of sample 304, its miniature features (or their absence) and metrology method. For example, cone angle χ can be between a fraction of a degree up to 5 degrees and the size of spot 320 can range from about 30 μm to 500 μm or more.

Apparatus 300 has a second detector 322 positioned below sample 304 for registering or detecting a transmitted response beam 324 composed of broadband radiation 302 transmitted through sample 304. More precisely, detector 322 is sensitive over a spectral range corresponding to wavelength range Δλ such that it can detect broadband radiation 302 that passes through sample 304.

An aperture 326 is provided for spatially filtering broadband radiation 302. In the present embodiment, aperture 326 is an entrance aperture placed before detector 322. A sampling aperture 328 is placed in the path of broadband test beam 116 between mirrors 312, 314 at the beam waist. The diameters of apertures 326, 328 are chosen to be sufficiently small to prevent broadband radiation 302 that undergoes multiple internal reflections in sample 304 from arriving at detector 322.

Apparatus 300 is configured to perform transmission measurements as well as reflection measurements. For this purpose, apparatus 300 has a second reflective optics 330 and corresponding first detector 332 with an entrance aperture 334 for performing reflectance measurements. These parts are indicated in dashed lines in FIG. 21.

FIG. 22A is a ray trace that visualizes the effects of entrance aperture 334 on the portion of reference test beam 316 that is received by detector 332 (sampling aperture 328 excluded). In this example, the diameter of aperture 334 is 50 μm, source 306 is 2 mm across, the angle of incidence is 7 degrees and sample 304 is 6.4 mm thick. The ray trace only shows rays of radiation 302 that arrive at detector 332. Note that the amount of radiation 302 that undergoes multiple internal reflections in sample 304 and still passes through aperture 334 to detector 332 is reduced significantly as compared to FIG. 1. In fact, only a small amount of radiation 302 undergoing a single internal reflection is able to get to detector 332.

FIG. 22B is a ray trace that shows the effect of entrance aperture 326 on the transmitted response beam 316 received by detector 322 after transmission through sample 104 (sampling aperture 328 excluded). The diameter of entrance aperture 326 is 50 μm, source 306 is 2 mm across, the angle of incidence is 7 degrees and sample 304 is a 6.4 mm thick fused quartz plate. Note that aperture 326 prevents most of radiation 302 undergoing multiple reflections in sample 304 from arriving at detector 322.

For best performance, both the sampling aperture and the entrance apertures should be used. Specifically, radiation 302 that is transmitted through sample 304 passes through entrance aperture 326 and sampling aperture 328. Reflected radiation 302 passes through apertures 328 and 334.

FIG. 23A is an optical ray trace illustrating the effects of sampling aperture 328 and entrance aperture 334 on reflected radiation 302 forming the reflected response beam. When sampling aperture 328 has a diameter of 1.0 mm or less and is placed at the waist of broadband test beam 316 or, equivalently, at the image of source 306 no backside reflected radiation 302 reaches detector 332. In other words, the presence of apertures 328 and 334 prevents radiation 302 undergoing multiple reflections within sample 304 from reaching detector 332.

FIG. 23B illustrates the effects of 1.0 mm sampling aperture 328 and entrance aperture 326 on transmitted radiation 302 arriving at detector 322. Note that the presence of sampling aperture 328 and entrance aperture 326 prevents multiply reflected radiation 302 from reaching detector 322. The ray trace of FIG. 23C summarizes the effects of apertures 326, 328 and 334 on radiation 302 that is reflected and transmitted producing the ideal situation where no radiation 302 that is internally reflected in sample 304 arrives at either detector 322 or detector 332. It should be noted that in alternative embodiments further apertures or pinholes can be used for spatial filtering.

Referring back to FIG. 21, we see that apparatus 300 further employs an optical compensator 336 for compensating the chromatic dispersion in transmitted response beam 324. In the present embodiment compensator 336 is a single fused quartz plate of a certain thickness relative to sample 304. Plate 336 is placed between sample 304 and detector 322, or more precisely between sample 304 and entrance aperture 326 of detector 322. Furthermore, plate 336 is also positioned at a certain tilt relative to sample 304.

To better understand how the parameters of thickness and tilt of plate 336 relative to sample 304 operate to compensate chromatic dispersion in transmitted response beam 324 we first refer to examples shown in FIGS. 24A-B. In these examples all optics are ideal and the source is a point source for better illustration. Similar results can be achieved with non-ideal optics and sources with proper choice of the mirrors and lenses and by using a source with a small spot.

FIG. 24A is a diagram illustrating a situation in which test beam 316 is incident normal to sample 304, rather than off-normal, as called for by the invention. Radiation 302 is focused to spot 320 on sample 304 by lens 314 acting as an ideal lens with a half-cone angle χ of 6 degrees. Sample 304 is 6.4 mm thick. Radiation 302 travels through sample 304 on its way to detector 322 and undergoes a certain amount of chromatic dispersion on its way. The chromatic dispersion is visualized in the image spot 320' of spot 320 formed by an ideal lens 338 (not shown in FIG. 21). Note that spot 320' covers almost 50 μm due to chromatic dispersion since rays of different wavelength have different focal lengths through plate 304. Spot 320' shows where rays of radiation 302 at three different wavelengths fall, namely at 190 nm (blue) indicated by "+", at 500 nm (green) indicated by "x" and at 900 nm (red) shown by squares. FIG. 24B illustrates how a low power positive lens, and more precisely a plano-convex lens 340 with its flat side facing sample 304 and its convex side facing lens 338 compensates for the chromatic dispersion. Now spot 320' of rays at the three chosen wavelengths is just a few nanometers in diameter; in fact, with appropriate curvature of lens 340 spot 320' can be diffraction limited for all wavelengths within wavelength range Δλ.

Figure 25A:
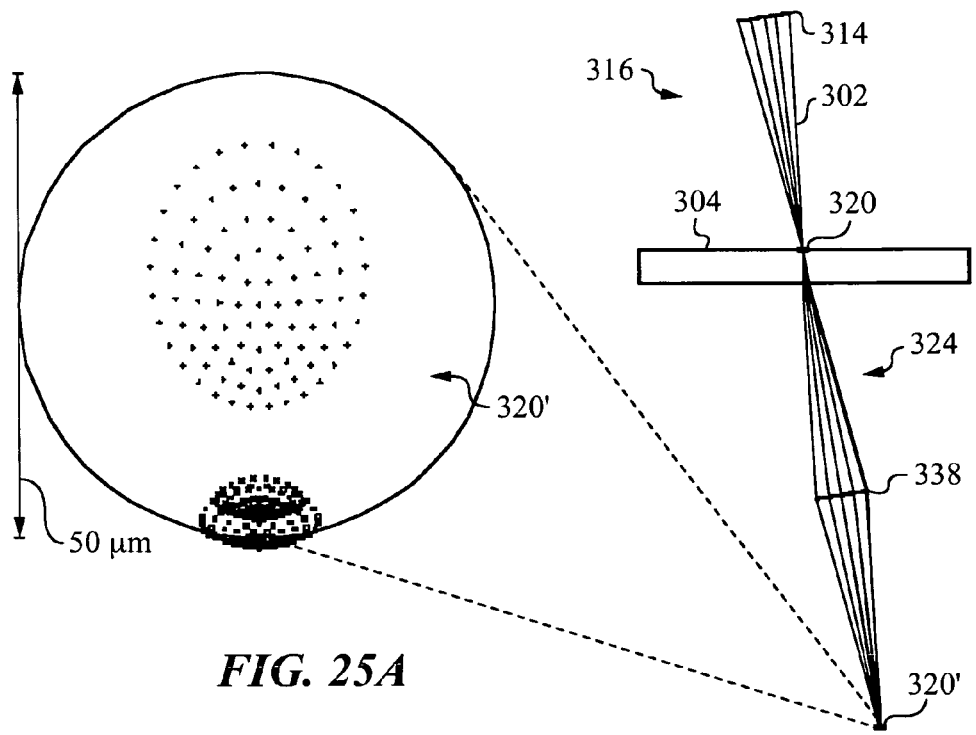

In practicing the invention, the angle of incidence is near normal but never normal. The situation arising at a 9 degree angle of incidence in the absence of plate 336 is shown in FIG. 25A. Note that chromatic dispersion causes a horizontal spreading or chromatic walk-off of rays at the three representative wavelengths at spot 320'. Although the sizes of individual spots at the three wavelengths are not very large, the overall spot 320' extends over close to 50 μm with the center of blue and red being separated by 25 μm. Therefore, when entrance aperture 326 of detector 322 is 30 μm in diameter, it will be very difficult to obtain a good signal in both short and long wavelength regions of wavelength range Δλ.

Figure 25B:
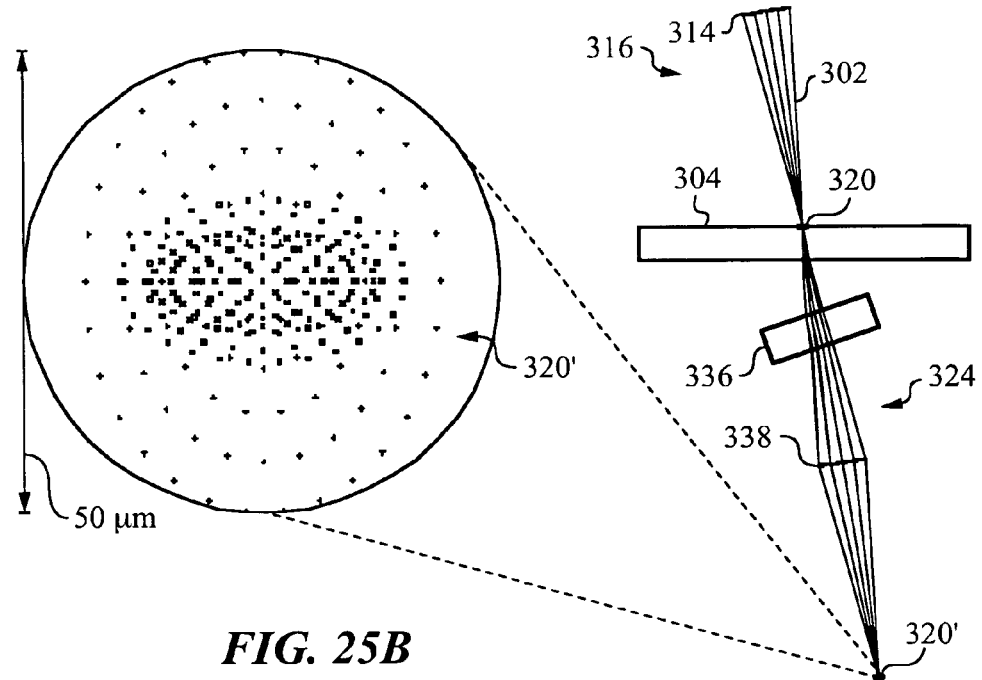

In accordance with the invention, plate 336 is placed between sample 304 and detector 322, and still more precisely before lens 338, as shown in FIG. 25B. To offset the chromatic dispersion, and more precisely to reverse the chromatic walk-off between different wavelengths, plate 336 is tilted in the opposite direction relative to sample 304, i.e., into the optical path. In other words, plate 336 is a diffused quartz plate of the same thickness as sample 304 and it is titled by the same angle as the angle of incidence, namely 9 degrees but in the opposite direction. Note that the centers or centroids of the three representative wavelengths now are coincident thus eliminating the chromatic walk-off.

Figure 25C:
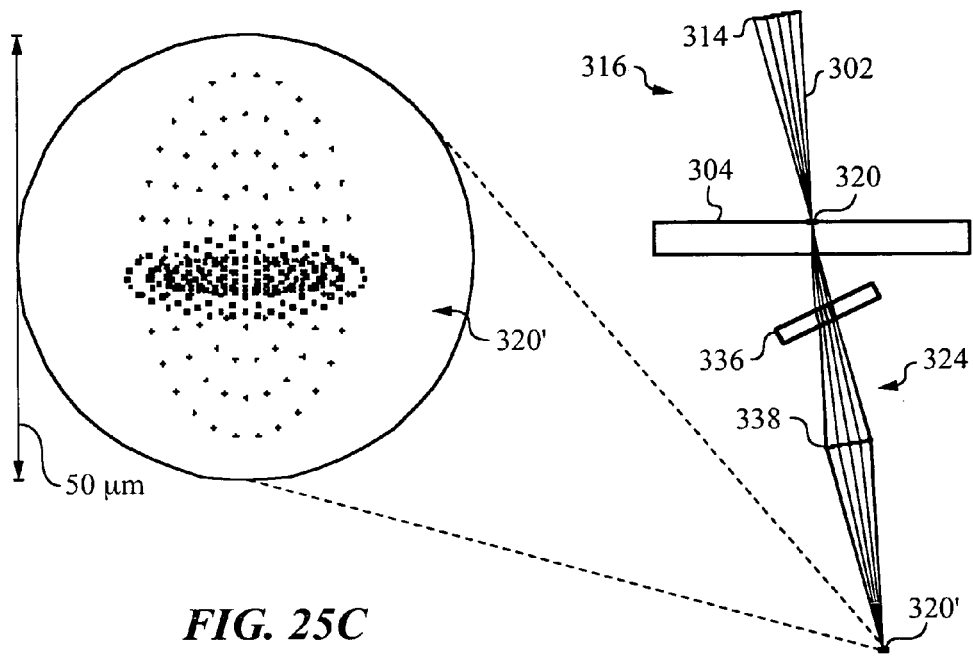

Further improvement in combating chromatic dispersion can be achieved by adjusting the thickness and tilt of plate 336 with respect to sample 304. FIG. 25C shows, for example, that when the thickness of plate 336 is adjusted to 3 mm and the optimized tilt angle is 17.4 degrees spot 320' exhibits no chromatic walk-off and also is smaller than in FIG. 25B. In other words, selecting these thickness and tilt parameters for plate 336 reduces chromatic dispersion due to chromatic aberration in addition to eliminating the chromatic dispersion due to chromatic walk-off.

Figure 25D:
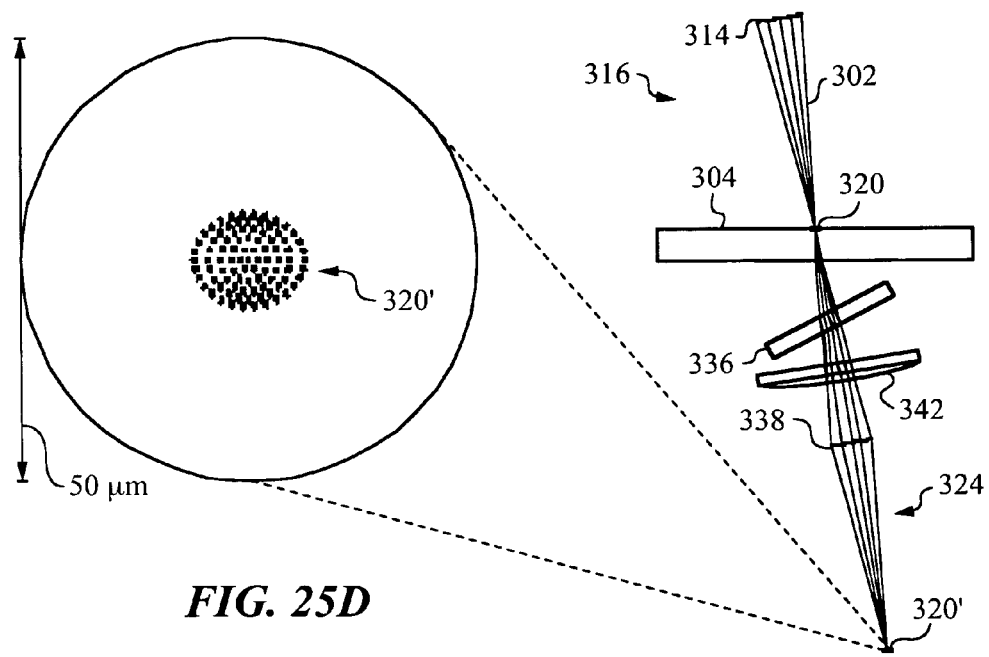

Still further improvement in the performance of apparatus 300 can be achieved by using plate 336 and a lens 342 as the optical compensator to compensate for chromatic dispersion due to chromatic aberration, as illustrated in FIG. 25D. Lens 342 is a low power positive diffused quartz lens (same material as that of plate 336) that is placed in the optical path of the transmitted portion of test beam 316 between plate 336 and lens 338. The axis of lens 342 is parallel to the chief ray of the transmitted beam portion in this case. In other words, lens 342 is tilted relative to sample 304. When the position, tilt and power of lens 342 are optimized, co-centricity and small spot-size 320' are obtained for all the wavelengths. In other words, both chromatic walk-off and chromatic aberration in spot 320' are largely reversed, as is clear from the figure.

Figure 25E:
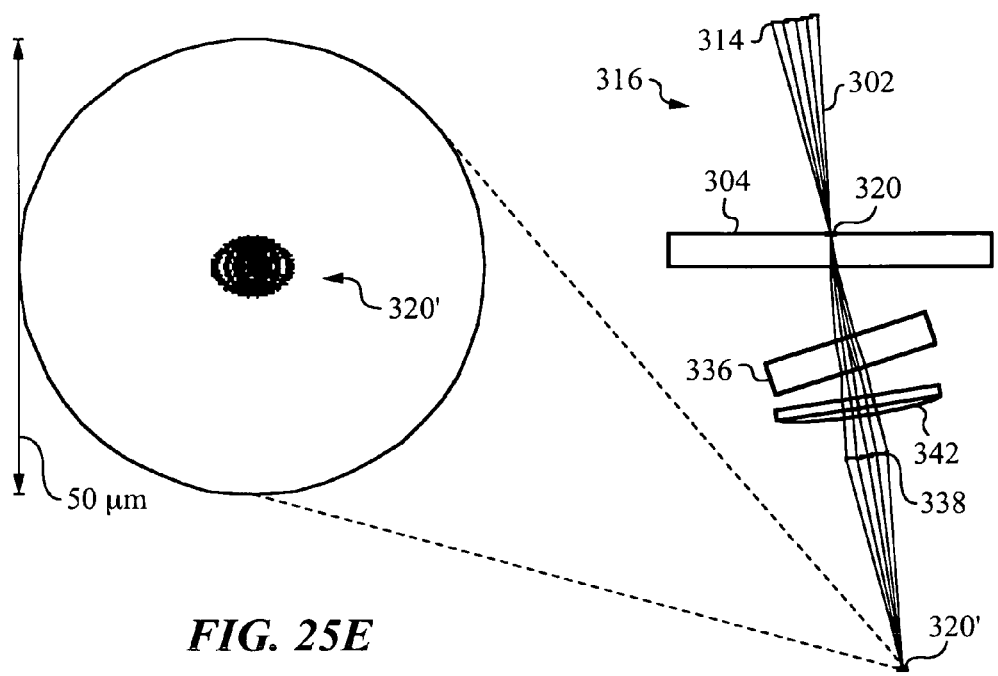
Figure 25F:
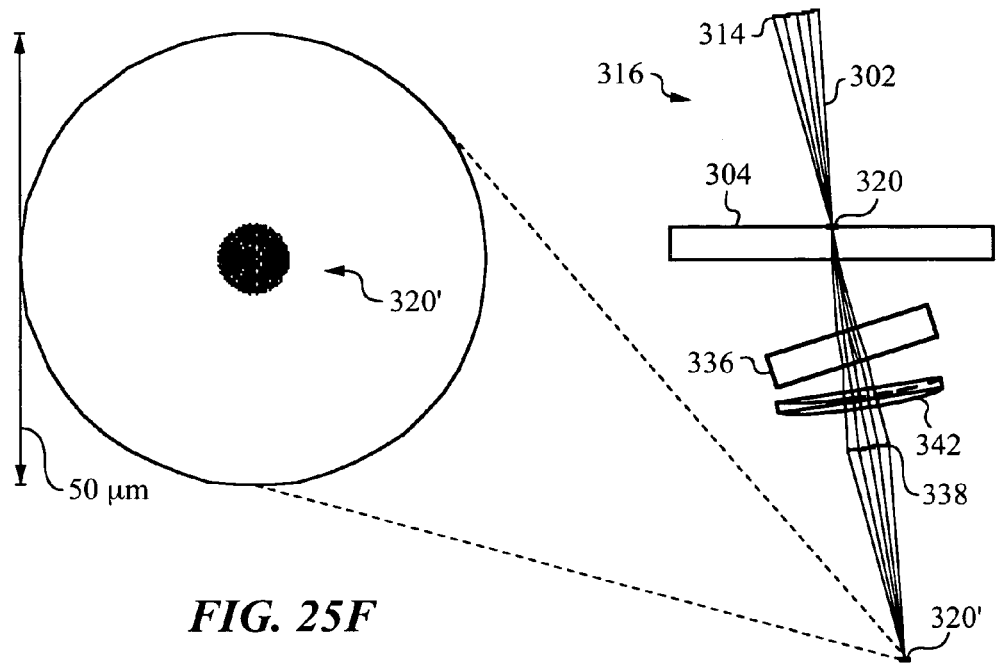

A better result in dispersion compensation can be obtained when plate 336 is made of the same material and has the same thickness as sample 304. This situation is shown in FIG. 25E. Lens 342 in this case can be a low power lens. Note how the change in the thickness of plate 304 has helped reduce the chromatic dispersion to produce a spot 320' that is almost one half the size of spot 320' in the embodiment of FIG. 25D. Even better result is obtained by selecting low power lens 342 to be a meniscus lens. The results for this embodiment are shown in FIG. 25F.

The apparatus of invention can be used to compensate for chromatic dispersion in various optical metrology applications including examination of material properties, critical dimensions (CDs) and profile determination of patterned sample surfaces. In fact, any application that requires the passage of a test beam through a plate that is transparent or semi-transparent can benefit from the present invention as soon as the thickness of the plate's thickness becomes significant, e.g., on the order of a millimeter or more.

In addition to yielding excellent wave front properties at the illuminated spot and compensating chromatic dispersion the apparatus and method of invention also provide for efficient beam monitoring. The monitoring can be employed in apparatus that performs either reflectance or transmittance measurements or both. The isometric view in FIG. 26 illustrates an apparatus 400 for performing optical metrology in reflectance mode and beam monitoring in accordance with the principles of the invention. Apparatus 400 has a compound broadband source 402 for providing broadband radiation 404 spanning a wavelength range $\Delta\lambda$. Radiation 404 is emitted in an output beam 406 toward a first reflective optics 408. Output beam 406 has a Gaussian beam profile or, in other words, the cross-section of output beam 406 is Gaussian.

Optics 408 have a pair of mirrors, namely a first toroidal mirror 410 and a second toroidal mirror 412. Various arrangements of toroidal mirrors 410, 412 are possible including parallel and crossed arrangements as described in the above embodiments. It will be appreciated by a person skilled in the art that optics 408 are not limited to two toroidal mirrors and can employ reflectors that have other curvature, such as, for example parabolic.

Mirrors 410, 412 are set up to intercept radiation 404 and shape it into a broadband test beam 414. In addition, mirrors 410, 412 cause broadband test beam 414 to converge to a first focus located between them and produce an image of source 402 in an image plane at a beam waist 416.

A sampling aperture 418 for filtering broadband test beam 414 is positioned in the image plane or at waist 416 between toroidal mirrors 410, 412. The size of aperture 418 is chosen so that a center portion 414A of test beam 414 is filtered or passed through aperture 418. When test beam 414 has a Gaussian cross-section, as in this preferred embodiment, center portion 414A should contain about 67% of the total intensity of test beam 414. In other words, filtered center portion 414A of beam 414 corresponds to radiation contained within the full width half maximum (FWHM) region or a single deviation from the maximum of the beam center or less.

Center portion 414A of test beam 414 is guided by optics 408 so that it impinges on a sample 420 at a spot 422. The size of spot 422 and cone angle $\chi$ of test beam 414 are selected based on sample 420 and its miniature features (or their absence) as well as the type of metrology method.

In accordance with the invention, sampling aperture 418 has a reflective region 419 surrounding aperture 418. Region 419 is provided for reflecting peripheral portion 414B of broadband test beam 414. Since center portion 414A containing 67% of the total intensity of test beam 414 is passed through aperture 418, reflective region 419 is preferably sufficiently large to reflect the remaining 33% of the total intensity of test beam 414. Thus, the amount of radiation that is used for monitoring purposes is not excessive and does not interfere with the production of high quality spot 422 having excellent wave front distribution.

A third detector 421 is placed near sampling aperture 418 for measuring peripheral portion 414B of broadband test beam 414 that is reflected by reflective region 419. A control unit 423 that is in communication with detector 421 and source 402 is used for monitoring broadband test beam 414 and adjusting source 402 based on peripheral portion 414B, e.g., based on its intensity over wavelength range $\Delta\lambda$.

A second reflective optics 424 is provided for shaping a reflected response beam 426 constituted by broadband radiation 404 that is reflected from sample 420 at spot 422. Second reflective optics 424 uses curved mirrors 428, 430 and a flat folding mirror 432 to deliver reflected response beam 426 to a first detector 434 for examination. Mirrors 428, 430 are two symmetrically placed parabolic mirrors that are off-axis such that they image spot 422 to first detector 434. An optional polarizer 436 is provided in the collimated portion of the beam path of reflected response beam 426 for performing polarization-dependent measurements.

During operation, apparatus 400 produces an excellent broadband test beam 414 and affords the user the ability to monitor fluctuations in the output of source 402. More specifically, the filtering of center portion 414A of beam 414 by sampling aperture 418 in conjunction with the use of toroidal mirrors 410, 412 ensures low chromatic aberrations as radiation 404 impinges at spot 422 on sample 420. Meanwhile, reflected peripheral portion 414B allows the user to contemporaneously monitor radiation 404 in broadband test beam 414.

In a preferred embodiment, control unit 423 adjusts the output of source 402 to ensure sufficient stability for the selected optical metrology method. The monitoring and adjustment process can take advantage of closed loop feedback techniques or any other control arrangements well-known to those skilled in the art. In cases where controlling source 402 could result in destabilization, the change in intensity or source drift is adjusted for numerically in the measurements obtained by first detector 434.

Apparatus 400 as illustrated in FIG. 26 does not make highly efficient use of reflected peripheral portion 414B of radiation 404. FIG. 27 shows how the addition of another optic 440 for shaping reflected portion 414B is used to better capture radiation 404. Preferably, optic 440 is an imaging optic, e.g., an imaging lens that images reflective region 419 on detector 421. Although in the present embodiment lens 440 is refractive, reflective optics can also be used.

In addition to optic 440, a beam splitter 442 is provided for separating sub-bands of peripheral portion 414B of radiation 404. Preferably, beam splitter 442 separates radiation 404 into sub-bands corresponding to those in which the individual sources making up compound broadband source 402 emit. For example, beam splitter 442 is a visible/ultra-violet (UV) beam splitter for separating the visible from the UV broadband radiation 404 in correspondence to the visible and UV emission spectra of the sources. In addition, separating radiation 404 into sub-bands ensures easier guidance and shaping of reflected radiation 404 (e.g., with refractive optics) as well as more reliable detection when using detectors only monitoring narrower portions or sub-bands of wavelength range $\Delta\lambda$.

Beamsplitter 442 separates wavelengths in the UV sub-band from visible wavelengths by any suitable technique. In the present case, beamsplitter 442 employs coatings that are well-known in the art. In these embodiments third detector 421 is compound, i.e., it has separate detection units 421A and 421B designed to individually detect radiation 404 in the corresponding sub-bands.

FIG. 28 illustrates in an isometric view an apparatus 500 that permits beam monitoring while studying a sample 520 that is semi-transparent. Apparatus 500 has a broadband source 502 for providing broadband radiation 504 spanning wavelength range $\Delta\lambda$. Sample 520 may be partly transparent over entire range $\Delta\lambda$ or just a portion thereof. Radiation 504 is emitted in an output beam 506 toward a first reflective optics 508. Preferably, output beam 506 has a Gaussian beam cross-section. Optics 508 employ a pair of toroidal mirrors 510, 512 for forming a broadband test beam 514 from output beam 506. As mentioned above, toroidal mirrors 510, 512 can be barrel or donut-shaped and they can be positioned in a crossed or parallel arrangement. In any of these arrangements, mirrors 510, 512 cause test beam 514 to converge and produce an image of source 502 in an image plane at a beam waist 516.

A sampling aperture 518 for filtering broadband test beam 514 is positioned in the image plane or at waist 516 between toroidal mirrors 510, 512. The size of aperture 518 is chosen so that a center portion 514A of test beam 514 is filtered or passed through aperture 518. When test beam 514 has a Gaussian cross-section, as in the preferred embodiment, center portion 514A should contain at most 67% of the total intensity of test beam 514. Center portion 514A of test beam 514 is guided by optics 508 so that it impinges on sample 520 at spot 522.

Sampling aperture 518 has a reflective region 519 for reflecting peripheral portion 514B of broadband test beam 514. Since center portion 514A containing 67% of the total intensity of test beam 514 is passed through aperture 518, reflective region 519 is preferably sufficiently large to reflect the remaining 33% of the total intensity of test beam 514.

A third detector 521, analogous to detector 421 that is described in FIG. 27 is placed near sampling aperture 518 for measuring peripheral portion 514B of broadband test beam 514 that is reflected by reflective region 519. In this embodiment, detector 521 is integrated with a control unit that is in communication with detector source 502 for adjusting the output of source 502 or, preferably, numerically correcting for source drift in the measurement.

Test beam 514, and more specifically its filtered center portion 514A is guided by optics 508 so that it impinges on a semi-transparent sample 520 at a spot 522. Depending on the nature of sample 520 (e.g., its material constitution and the presence or absence of miniature features) and the metrology method, mirrors 510, 512 and aperture 518 are chosen to achieve the appropriate cone angle $\chi$ and size of spot 522. The angle of incidence of test beam 514 is preferably steep such that test beam 514 is incident slightly off-normal on sample 520.

Apparatus 500 has a second detector 524 positioned below sample 520 for registering or detecting a transmitted response beam 526 of broadband radiation 504 transmitted through sample 520. More precisely, detector 524 is sensitive over a spectral range corresponding to wavelength range $\Delta\lambda$ such that it can detect broadband radiation 504 that passes through sample 520.

A second reflective optics 528 is provided for shaping a reflected response beam 529 constituted by broadband radiation 504 that is reflected from sample 520 at spot 522. Second reflective optics 528 uses a single curved mirror 530 to deliver response beam 529 to a first detector 532 for examination. Preferably, mirror 530 is a curved mirror that that images spot 522 to first detector 532. An optional aperture 534 is provided in the beam path of response beam 529 for performing additional spatial filtering.

Although in most cases it is only necessary to monitor source 502 it may, in some embodiments be useful to also monitor the reflected or transmitted radiation. Thus, in accordance with the invention, aperture 534 may be employed in monitoring reflected response beam 529 by reflecting a peripheral portion of beam 529 to a corresponding detector (not shown). Likewise, transmitted response beam 526 can be apertured and monitored in a similar manner if desired.

FIGS. 29 and 30 illustrate an alternative embodiment of an apparatus 600 that employs analogous second optics 602 and third optics 604 for guiding a reflected response beam 606 and a transmitted response beam 608 obtained from illuminating a sample 610 with a broadband test beam 612. Specifically, second optics 602 use two parabolic mirrors 614, 616 and third optics 604 also employ two parabolic mirrors 618, 620. As in the previous embodiments, a first optics 622 has two toroidal mirrors 624, 626 and a sampling aperture 628 placed between them for shaping and guiding test beam 612.

Apparatus 600 has a single tilted lens 630 for compensating the chromatic aberration encountered in transmitted response beam 608. This approach is not as effective as the above-taught solution employing a tilted plate and a lens, but is sufficient in cases where sample 610 is not very thick or chromatic aberration is not severe for other reasons.

Apparatus 600 also has a polarizer 632 incorporated in second optics 602 and a polarizer 634 in third optics 604 for performing polarization-based measurements.

The various embodiments of the apparatus and methods of invention take advantage of all-reflective optics and apertures to obtain low chromatic aberration. In addition, they leverage the function of the aperture or apertures in a novel way to simultaneously permit direct monitoring of the broadband beam. For this reason, the apparatus and method of invention are particularly well-suited in optical metrology requiring precise control over the incident and reflected radiation, such as optical scatterometry.

Clearly, the apparatus and method of invention can be employed in many situations. The wide spectral band and small spot size are key for many metrology applications including, among other, examination of semiconductor wafers and optical characterization of material parameters. Therefore, the scope of the invention should be judged by the appended claims and their legal equivalents.

I claim:

1. An apparatus for examining a sample with a broadband radiation, said apparatus comprising:
   a) a broadband source providing said broadband radiation spanning a wavelength range $\Delta\lambda$;
   b) a first reflective optics for shaping said broadband radiation into a broadband test beam incident on said sample at a spot and for adjusting a cone angle $\chi$ of said broadband test beam;
   c) a sampling aperture for filtering a predetermined center portion from said broadband test beam;
   d) a second reflective optics for shaping a reflected response beam of said broadband radiation reflected from said spot; and
   e) a first detector for examining said reflected response beam.

2. The apparatus of claim 1, wherein said first reflective optics comprises two crossed toroidal mirrors.

3. The apparatus of claim 2, wherein said sampling aperture is positioned between said two crossed toroidal mirrors.

4. The apparatus of claim 2, wherein said two crossed toroidal mirrors are selected from the group consisting of barrel-shaped toroidal mirrors and donut-shaped toroidal mirrors.

5. The apparatus of claim 1, wherein said second reflective optics comprises two parallel toroidal mirrors.

6. The apparatus of claim 5, wherein said sampling aperture is positioned between said two parallel toroidal mirrors.

7. The apparatus of claim 5, wherein said two parallel toroidal mirrors are selected from the group consisting of barrel-shaped toroidal mirrors and donut-shaped toroidal mirrors.

8. The apparatus of claim 1, wherein said second reflective optics further comprises two symmetrically placed off-axis parabolic mirrors for imaging said spot at said detector.

9. The apparatus of claim 1, wherein said broadband test beam has a Gaussian cross-section.

10. The apparatus of claim 9, wherein said predetermined center portion contains at most 67% of the intensity of said broadband test beam.

11. The apparatus of claim 1, wherein said broadband source is compound and said wavelength range $\Delta\lambda$ extends at least from ultra-violet to infra-red.

12. The apparatus of claim 11, wherein said broadband source comprises a set of individual sources spanning sub-bands of said wavelength range $\Delta\lambda$.

13. The apparatus of claim 1, further comprising:
   a) a third optics for shaping a transmitted response beam of said broadband radiation transmitted through said sample at said spot;
   b) a second detector for examining said transmitted response beam;
   wherein said predetermined center portion filtered from said broadband test beam by said sampling aperture is sufficiently small to prevent broadband radiation undergoing multiple internal reflections in sample from arriving at said second detector.

14. The apparatus of claim 13, further comprising an optical compensator placed between said sample and said second detector for compensating a chromatic dispersion of said broadband radiation transmitted through said sample.

15. The apparatus of claim 14, wherein said optical compensator comprises an optical plate positioned at a predetermined tilt relative to said sample.

16. The apparatus of claim 15, wherein said optical compensator further comprises a lens.

17. The apparatus of claim 16, wherein said lens is tilted relative to said sample.

18. The apparatus of claim 15, wherein said optical plate has a predetermined thickness relative to said sample.

19. The apparatus of claim 13, wherein said sampling aperture is placed in the path of said broadband test beam and an entrance aperture is placed before said second detector.

20. The apparatus of claim 1, further comprising;
   a) a reflective region surrounding said sampling aperture for reflecting a predetermined peripheral portion of said broadband test beam;
   b) a third detector for measuring said peripheral portion; and
   c) a control unit in communication with said third detector and monitoring said broadband test beam.

21. The apparatus of claim 20, wherein said control unit numerically corrects a drift of said broadband source.

22. The apparatus of claim 20, further comprising an optic for shaping said predetermined peripheral portion of said broadband test beam.

23. The apparatus of claim 22, wherein said optic is an imaging optic for imaging said reflective region on said third detector.

24. The apparatus of claim 20, further comprising a beam splitter for separating sub-bands of said wavelength range $\Delta\lambda$ in said predetermined peripheral portion.

25. The apparatus of claim 24, wherein said beam splitter is a visible/ultra-violet beam splitter.

26. The apparatus of claim 24, wherein said broadband source comprises a set of individual sources spanning said sub-bands.

27. The apparatus of claim 20, wherein said broadband test beam has a Gaussian cross-section and said predetermined peripheral portion contains at most 33% of the intensity of said broadband test beam.

28. A method for examining a sample with a broadband radiation spanning a wavelength range $\Delta\lambda$, said method comprising:
   a) producing said broadband radiation;
   b) shaping said broadband radiation into a broadband test beam by reflection from a first reflective optics such that said broadband test beam is incident on said sample at a spot with a cone angle $\chi$;
   c) filtering a predetermined center portion from said broadband test beam with a sampling aperture;
   d) shaping a reflected response beam of said broadband radiation reflected from said spot with a second reflective optics;
   e) detecting said reflected response beam; and
   f) providing a signal relating to said reflected response beam as an output.

29. The method of claim 28, wherein said first reflective optics comprise two toroidal mirrors and said filtering is performed at a broadband beam waist between said two toroidal mirrors.

30. The method of claim 28, wherein said second reflective optics comprise two parabolic mirrors and said method comprises placing said two parabolic mirrors symmetrically off-axis for imaging said spot at said detector.

31. The method of claim 28, further comprising polarization filtering.

32. The method of claim 28, further comprising:
   a) shaping a transmitted response beam of said broadband radiation transmitted through said sample at said spot;
   b) detecting said transmitted response beam; and
   c) providing a signal relating to said transmitted response beam as an output;
   wherein said predetermined center portion filtered from said broadband test beam by said sampling aperture is sufficiently small to prevent broadband radiation undergoing multiple internal reflections in said sample from arriving at said second detector.

33. The method of claim 32, wherein said step of filtering is performed by said sampling aperture and an entrance aperture.

34. The method of claim 32, further comprising compensating a chromatic dispersion in said broadband radiation transmitted through said sample by reversing a chromatic walk-off.

35. The method of claim 34, wherein said chromatic walk-off is reversed by providing an optical plate oriented at a predetermined tilt relative to said sample.

36. The method of claim 35, wherein said optical plate is selected to have a predetermined thickness relative to said sample.

37. The method of claim 32, further comprising compensating a chromatic dispersion in said broadband radiation transmitted through said sample by reversing a chromatic aberration.

38. The method of claim 37, wherein said chromatic aberration is reversed with a lens.

39. The method of claim 28, further comprising:
   a) surrounding said sampling aperture with a reflective region to reflect a predetermined peripheral portion of said broadband test beam;
   b) measuring said peripheral portion; and
   c) monitoring said broadband test beam based on said peripheral portion.

40. The method of claim 39, further comprising closed loop feedback to a broadband source of said broadband radiation.

41. The method of claim 39, wherein said broadband test beam has a Gaussian cross-section and said method comprises reflecting at most 33% of the intensity of said broadband test beam by said reflective region.

42. A metrology system comprising an apparatus for examining a sample with a broadband radiation spanning a wavelength range $\Delta\lambda$, said apparatus comprising:
   a) a broadband source producing said broadband radiation;
   b) a first reflective optics for shaping said broadband radiation into a broadband test beam incident on said sample at a spot and with a cone angle $\chi$;
   c) a sampling aperture for filtering a predetermined center portion of said broadband test beam;
   d) a second reflective optics for shaping a reflected response beam of said broadband radiation reflected from said spot; and
   e) a detector for examining said reflected response beam.

43. The metrology system of claim 42, wherein said first reflective optics comprises toroidal mirrors selected from the group consisting of barrel-shaped toroidal mirrors and donut-shaped toroidal mirrors.

44. The metrology system of claim 42, further comprising:
   a) a third optics for shaping a transmitted response beam of said broadband radiation transmitted through said sample at said spot;
   b) a second detector for examining said transmitted response beam;
   wherein said predetermined center portion filtered from said broadband test beam by said sampling aperture is sufficiently small to prevent broadband radiation undergoing multiple internal reflections in said sample from arriving at said second detector.

45. The metrology system of claim 44, further comprising an optical compensator placed between said sample and said second detector for compensating a chromatic dispersion of said broadband radiation transmitted through said sample.

46. The metrology system of claim 42, further comprising:
   a) a reflective region surrounding said sampling aperture for reflecting a predetermined peripheral portion of said broadband test beam;
   b) a third detector for measuring said peripheral portion; and
   c) a control unit being in communication with said third detector and monitoring said broadband test beam.

* * * * *